(12) United States Patent
Kobayashi et al.

(10) Patent No.: US 6,528,514 B1
(45) Date of Patent: Mar. 4, 2003

(54) IGE ANTIBODY PRODUCTION INHIBITORS AND AUTOIMMUNE DISEASES INHIBITORS

(75) Inventors: Fujio Kobayashi, Osaka (JP); Shigeki Kuwahara, Osaka (JP); Naruyasu Komorita, Osaka (JP); Koji Naito, Osaka (JP); Teruaki Imada, Osaka (JP); Tsutomu Yoshikawa, Osaka (JP)

(73) Assignee: Welfide Corporation, Osaka (JP)

(*) Notice: Subject to any disclaimer, the term of this patent is extended or adjusted under 35 U.S.C. 154(b) by 0 days.

(21) Appl. No.: 09/646,388

(22) PCT Filed: Mar. 10, 1999

(86) PCT No.: PCT/JP99/01148

§ 371 (c)(1),
(2), (4) Date: Dec. 20, 2000

(87) PCT Pub. No.: WO99/45928

PCT Pub. Date: Sep. 16, 1999

(30) Foreign Application Priority Data

Mar. 11, 1998 (JP) .......................................... 10-080354
Mar. 27, 1998 (JP) .......................................... 10-100361

(51) Int. Cl.[7] ..................... A61K 31/505; C07D 239/02; C07D 401/00; A61P 37/08
(52) U.S. Cl. ..................... 514/269; 514/321; 514/322; 514/324; 514/326; 514/331; 544/319; 544/362; 544/364; 544/366; 544/367; 544/382
(58) Field of Search ............................... 514/321, 322, 514/324, 326, 331, 269; 544/362, 364, 366, 367, 382, 319

(56) References Cited

U.S. PATENT DOCUMENTS

| | | | |
|---|---|---|---|
| 5,441,960 A | | 8/1995 | Bernstein et al. |
| 5,596,111 A | | 1/1997 | Sibi et al. |
| 5,948,785 A | * | 9/1999 | Akahoshi et al. ............ 514/269 |
| 6,080,738 A | * | 6/2000 | Akahoshi et al. ......... 514/227.8 |

FOREIGN PATENT DOCUMENTS

| | | |
|---|---|---|
| EP | 0 509 769 A2 | 10/1992 |
| EP | 0 528 633 A1 | 2/1993 |
| EP | 0 826 671 A1 | 3/1998 |
| JP | 07295899 | 10/1995 |
| JP | 10-7661 * | 1/1998 |
| JP | 10-53579 | 2/1998 |
| WO | WO 96/33974 | 10/1996 |
| WO | WO 98/09949 | 3/1998 |
| WO | WO 98/18794 | 5/1998 |
| WO | WO99/26925 A1 | 3/1999 |

OTHER PUBLICATIONS

Sho Matsushita, et al. "Purification of murine suppressive factor of allergy into distinct CD23-modulating and IgE-suppressive proteins" Proc. Natl. Acad. Sci. USA vol. 88, pp. 4718–4722, Jun. 1991 Immunology.

Sho Matsushita et al. The Murine e Receptor Modulating Protein: A Novel Serine Protease Which Modulates CD23 Binding of IgE[1]. Cellular Immunology 137,252–259 (1991).

Sho Matsushita, et al. Short Communications Biphasic Effect of Kaliikrein on IgE and 1gG1 Syntheses by LPS/1L–4–Stimulated B Cells[1] Cellular Immunology 146, 210–214 (1993).

Makoto Iwata, et al. Modulation of the Biologic Activities of IgE–Binding Factor IV. Identification of Glycosylation–enhancing Factor as a Kallikrein–like Enzyme[1] The Journal of Immunology vol. 131, No. 4, 1954–1960 Oct. 1983.

Kimishige Ishizaka "IgE–Binding Factors and Regulation of the IgE Antibody Response" Ann. Rev. Immunol. 1988 vol. 6, pp. 513–534.

I. Kamata et al. "Cysteine protease of the Nematode *Nippostrongylus brasilensis* preferentially evokes an IgE/IgG1 antibody response in rats" Clin. Exp. Immunol 1995, vol. 102, pp. 71–77.

Holgate, Stephen T.: "The immunopharmacology of mild ssthma," Journal of Allergy and Clinical Immunology, (1996) vol. 98, No. 5, Part 2, pp. S7–S16.

Katunuma N et al.: "Biological Functions of Serine Proteases in Mast Cells in Allergic Inflammation,"0 J. Cell. Biochem., (1988) 38 (4), 291–302.

Dietze S C et al.: "Inhibition of Histamine Release from Human Mast Cells Ex–Vivo by Natural and Synthetic Chymase Inhibitors." 2nd International Symposium on Proteinase Inhibit and Biological Control, BRDO, Yugoslavia, Jun. 25–28, 1989 Biol Chem Hoppe–Seyler, (1990) 371 (Supple), 75–80.

Kido H et al.: "Antibody and Inhibitor of Chymase Inhibit Histamine Release in Immunolobulin E–Actived Mast Cells." Biochem Int, (1985) 10 (6), 863–872.

* cited by examiner

Primary Examiner—Mukund J. Shah
Assistant Examiner—Tamthom N. Truong
(74) Attorney, Agent, or Firm—Sughrue Mion, PLLC

(57) ABSTRACT

The present invention relates to an IgE antibody production inhibitor and an autoimmune disease suppressant containing a heterocyclic amide compound represented by the following general formula (1) or a pharmaceutically acceptable salt thereof as an active ingredient (1)

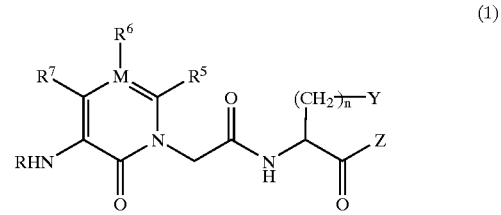

wherein R represents a hydrogen atom, alkyl, —CHO, —COOH, etc.; $R^5$, $R^6$ and $R^7$ represent each hydrogen, alkyl, aryl, etc.; M represents a carbon atom or a nitrogen atom; Y represents aryl, etc.; and Z represents hydrogen, alkyl, aryl, etc.

10 Claims, 2 Drawing Sheets

IGE ANTIBODY PRODUCTION INHIBITORS AND AUTOIMMUNE DISEASES INHIBITORS

TECHNICAL FIELD

The present invention relates to an IgE antibody production inhibitor and an autoimmune disease suppressant which are characterized by comprising a heterocyclic amide compound having a specific structure or a pharmaceutically acceptable salt thereof as an active ingredient.

BACKGROUND ART

The incidence of allergic diseases such as bronchial asthma, allergic rhinitis, allergic dermatitis, etc. has been increasing remarkably in recent years and is a serious social concern today. These allergic diseases are classified as Type I allergic reaction and the mechanism of pathogenesis of these diseases is suspected to be as follows.

Namely, in the first phase, the invasion of an antigen into the body results in interactions of macrophages, T cells, B cells, etc. causing production of an IgE antibody which is closely involved in Type I allergic reaction and the body is sensitized as this IgE antibody is bound to the receptors on tissue mast cells or blood basophils. In the second phase that ensues, the antigen reinvading the body attaches to the IgE antibody bound to the receptors and the resulting antigen-antibody reaction triggers a degranulation causing an extracellular release of various mediators such as histamine, SRS-A, etc. Further, in the third phase, the released mediators induce various allergic reactions owing to their smooth muscle-contacting action, vascular permeability-enhancing action, secretion-stimulating action and the like.

Many of the therapeutic agents and prophylactic agents for allergic diseases which have been developed and put on the market are drugs acting on the above-mentioned second phase or third phase. Since the basic cause of allergic diseases is the production of IgE antibodies in the body, any drug which could inhibit or suppress the production of IgE antibodies should be expected to have a remarkable efficacy for radical therapy in light of the above mechanism of pathogenesis.

Furthermore, in many cases, autoimmune diseases such as systemic lupus erythematosus, Hashimoto's thyroiditis, myasthenia gravis, rheumatoid arthritis, Guillain-Barré syndrome, glomerulonephritis, systemic erythematosus, etc. accompany an abnormal regulation of cellular immunity and humoral immunity and are associated with an abnormality or enhancement of the effector function of T cells, B cells and macrophages which is directed to autoantigens in the blood. The activation of such cellular components against autoantigens is considered to be related to the derangement of the feedback system relevant to autogenous resistance.

An autoimmune disease produces symptoms in one or more specific sites of the various organs of the body but is characterized in that such symptoms have much in common in the multiple sites. Moreover, there is a characteristic tendency that these symptoms are invariably chronic, subside unaccountably at times or flare up spontaneously, and are even associated with symptoms in other organs in the manner of a chain reaction.

It is generally acknowledged that such autoimmune diseases cause the appearance of autoantibodies in the blood, inappropriate Class II antigen expression, macrophage activation, and T-cell infiltration into target organs, and the like. However, the trigger mechanism involved in the activation of autoimmune diseases has not been made clear, nor has the mechanism of progression of autoimmune diseases been elucidated. Therefore, both prophylactic and therapeutic methods are still in quite unsatisfactory state today.

For suppressing of autoimmune diseases, various therapeutic methods inclusive of administration of drugs such as gold salts, methotrexate, antimalarials, glucocorticoids (e.g. methylprednisolone), etc.; plasmapheresis; resistance induction, etc. have been attempted but in efficacy as well as in terms of side effects, none have proved satisfactory enough.

There is an urgent need, therefore, for the development of drugs which could suppress autoimmune diseases with little risk for side effects.

SUMMARY OF THE INVENTION

In the above state of the art, the present invention has an object to provide a pharmaceutically useful IgE antibody production inhibitor comprising a substance having IgE antibody production inhibitory action as an active ingredient. A further object of the invention, in the above state of the art, is to create an entirely new autoimmune disease suppressant.

The first aspect of the present invention is an IgE antibody production inhibitor comprising a heterocyclic amide compound of the following general formula (1) or a pharmaceutically acceptable salt thereof as an active ingredient;

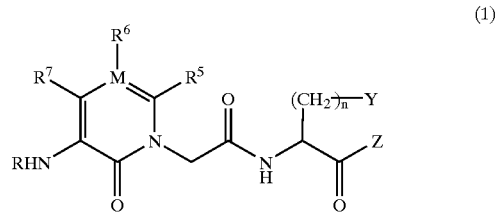

(1)

wherein R represents a hydrogen atom, alkyl, —CHO, —COOH, —CONH$_2$, —COR$^1$, —COOR$^1$, —CONHOR$^1$, —CONHR$^1$, CONR$^1$R$^{1'}$, —CONHSO$_2$R$^1$, —COSR$^1$, —COCOR$^2$, —COCOOR$^2$, —CONHCOOR$^2$, —COCONR$^3$R$^4$, —CSXR$^1$, —SO$_2$WR$^1$, —SO$_2$NR$^1$R$^{1'}$, or —SO$_2$E;

R$^1$ and R$^{1'}$ may be the same or different and each represents alkyl, cycloalkyl, cycloalkylalkyl, aryl, arylalkyl, heteroaryl, heteroarylalkyl, heterocycle or heterocyclic alkyl;

R$^2$, R$^3$ and R$^4$ may be the same or different and each represents a hydrogen atom, alkyl or arylalkyl, or R$^3$ and R$^4$ of —NR$^3$R$^4$ may be combined each other to form a heterocycle;

X represents a single bond, an oxygen atom, a sulfur atom, or —NH—;

W represents a single bond, —NH—, —NHCO—, —NHCOO— or —NHCONH—;

E represents hydroxyl group or amino;

R$^5$, R$^6$ and R$^7$ may be the same or different and each represents a hydrogen atom or alkyl, or one of R$^5$, R$^6$ and R$^7$ represents aryl, arylalkyl, arylalkenyl, heteroaryl, heteroarylalkyl or heteroarylalkenyl, with each of the remaining two representing a hydrogen atom;

M represents a carbon atom or a nitrogen atom and when M represents a nitrogen atom, R$^6$ does not exist;

Y represents cycloalkyl, aryl or heteroaryl;

Z represents a hydrogen atom, —$CF_2R^8$, —$CF_2CONR^9R^{10}$, —$CF_2COOR^9$, —$COOR^9$, —$CONR^9R^{10}$, a group of the following formula (i), a group of the following formula (ii), or a group of the following formula (iii);

$R^8$ represents a hydrogen atom, halogen, alkyl, perfluoroalkyl, aminoalkyl, alkylaminoalkyl, dialkylaminoalkyl, alkoxyalkyl, hydroxyalkyl, aryl, arylalkyl, arylalkenyl, heteroaryl, heteroarylalkyl or heteroarylalkenyl; $R^9$ and $R^{10}$ may be the same or different and each represents a hydrogen atom, alkyl, alkenyl, cycloalkyl, cycloalkylalkyl, heterocyclic alkyl, aryl, arylalkyl, arylalkenyl, heteroaryl, heteroarylalkyl or heteroarylalkenyl, or $R^9$ and $R^{10}$ of —$NR^9R^{10}$ may be combined each other to form a heterocycle;

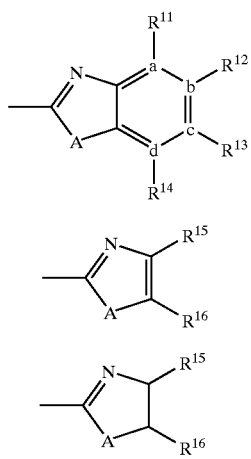

wherein a, b, c and d respectively represents a carbon atom or one of a, b, c and d represents a nitrogen atom with each of the remaining three representing a carbon atom;

$R^{11}$, $R^{12}$, $R^{13}$ and $R^{14}$ may be the same or different and each represents a hydrogen atom, alkyl, aryl, arylalkyl, heteroaryl, heteroarylalkyl, halogen, trifluoromethyl, cyano, nitro, —$N^{17}R^{17'}$, —$NHSO_2R^{17}$, —$OR^{17}$, —$COOR^{17}$, —$CONHSO_2R^{17}$ or —$CONR^{17}R^{17'}$; provided that when one of a, b, c and d represents a nitrogen atom, $R^{11}$, $R^{12}$, $R^{13}$ or $R^{14}$ combined to the nitrogen atom mentioned for a, b, c or d does not exist;

$R^{15}$ and $R^{16}$ may be the same or different and each represents a hydrogen atom, alkyl, aryl, arylalkyl, heteroaryl, heteroarylalkyl, halogen, trifluoromethyl, cyano, nitro, —$NR^{17}R^{17'}$, —$NHSO_2R^{17}$, —$OR^{17}$, —$COOR^{17}$, —$CONHSO_2R^{17}$ or —$CONR^{17}R^{17'}$;

$R^{17}$ and $R^{17'}$ maybe the same or different and each represents a hydrogen atom, alkyl, cycloalkyl, cycloalkylalkyl, aryl, arylalkyl, heteroaryl, heteroarylalkyl or trifluoromethyl, or $R^{17}$ and $R^{17'}$ of —$NR^{17}R^{17'}$ may be combined each other to form a heterocycle;

A represents an oxygen atom, a sulfur atom or —$NR^{18}$—; $R^{18}$ represents a hydrogen atom, alkyl, cycloalkyl or cycloalkylalkyl;

n represents 0 or 1;

said alkyl, cycloalkyl, cycloalkylalkyl, aryl, arylalkyl, arylalkenyl, heteroaryl, heteroarylalkyl, heteroarylalkenyl, heterocycle and heterocyclic alkyl may be substituted by one or more substituents respectively.

In the preferred embodiment of the first aspect of the present invention, said IgE antibody production inhibitor is a prophylactic agent for bronchial asthma, a prophylactic agent for allergic rhinitis, a prophylactic agent for allergic dermatitis, a therapeutic agent for bronchial asthma, a therapeutic agent for allergic rhinitis, or a therapeutic agent for allergic dermatitis.

The second aspect of the present invention is an autoimmune disease suppressant comprising a heterocyclic amide compound of the above general formula (1) or a pharmaceutically acceptable salt thereof as an active ingredient.

In the preferred embodiment of the second aspect of the present invention, said autoimmune disease suppressant is a prophylactic agent for systemic lupus erythematosus, a prophylactic agent for Hashimoto's thyroiditis, a prophylactic agent for myasthenia gravis, a prophylactic agent for rheumatoid arthritis, a prophylactic agent for Guillain-Barré syndrome, a prophylactic agent for glomerulonephritis, a prophylactic agent for systemic erythematosus, a therapeutic agent for systemic lupus erythematosus, a therapeutic agent for Hashimoto's thyroiditis, a therapeutic agent for myasthenia gravis, a therapeutic agent for rheumatoid arthritis, a therapeutic agent for Guillain-Barré syndrome, a therapeutic agent for glomerulonephritis or a therapeutic agent for systemic erythematosus.

DISCLOSURE OF INVENTION

Figure 1:
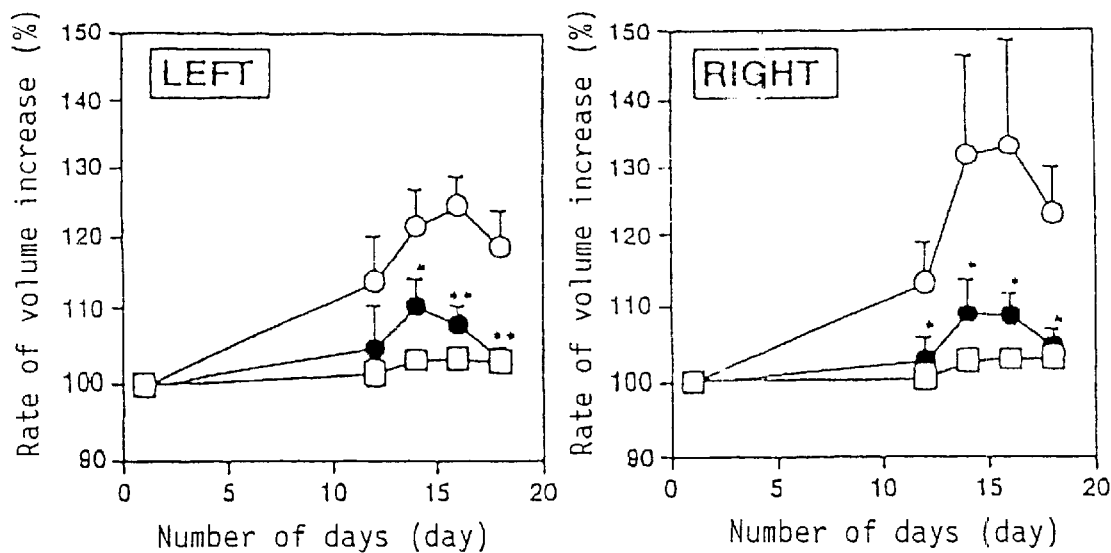
FIG. 1 is a diagram showing the antiarthritic effect (hind paw volume) found in Test Example 2.

The first aspect of the present invention is an IgE antibody production inhibitor comprising a heterocyclic amide compound of the following general formula (1) or a pharmaceutically acceptable salt thereof as an active ingredient;

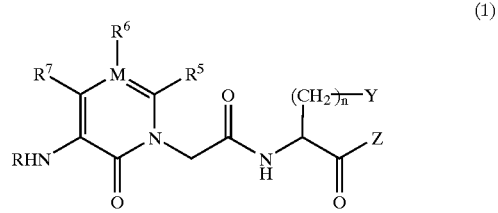

wherein R represents a hydrogen atom, alkyl, —CHO, —COOH, —$CONH_2$, —$COR^1$, —$COOR^1$, —$CONHOR^1$, —$CONHR^1$, $CONR^1R^{1'}$, —$CONHSO_2R^1$, —$COSR^1$, —$COCOR^2$, —$COCOOR^2$, —$CONHCOOR^2$, —$COCONR^3R^4$, —$CSXR^1$, —$SO_2WR^1$, —$SO_2NR^1R^{1'}$ or —$SO_2E$;

$R^1$ and $R^{1'}$ may be the same or different and each represents alkyl, cycloalkyl, cycloalkylalkyl, aryl, arylalkyl, heteroaryl, heteroarylalkyl, heterocycle or heterocyclic alkyl;

R², R³ and R⁴ may be the same or different and each represents a hydrogen atom, alkyl or arylalkyl, or R³ and R⁴ of —NR³R⁴ may be combined each other to form a heterocycle;

X represents a single bond, an oxygen atom, a sulfur atom, or —NH—;

W represents a single bond, —NH—, —NHCO—, —NHCOO— or —NHCONH—;

E represents hydroxyl group or amino;

R⁵, R⁶ and R⁷ may be the same or different and each represents a hydrogen atom or alkyl, or one of R⁵, R⁶ and R⁷ represents aryl, arylalkyl, arylalkenyl, heteroaryl, heteroarylalkyl or heteroarylalkenyl, with each of the remaining two representing a hydrogen atom;

M represents a carbon atom or a nitrogen atom and when M represents a nitrogen atom, R⁶ does not exist;

Y represents cycloalkyl, aryl or heteroaryl;

Z represents a hydrogen atom, —CF₂R⁸, —CF₂CONR⁹R¹⁰, —CF₂COOR⁹, —COOR⁹, —CONR⁹R¹⁰, a group of the following formula (i), a group of the following formula (ii), or a group of the following formula (iii);

R⁸ represents a hydrogen atom, halogen, alkyl, perfluoroalkyl, aminoalkyl, alkylaminoalkyl, dialkylaminoalkyl, alkoxyalkyl, hydroxyalkyl, aryl, arylalkyl, arylalkenyl, heteroaryl, heteroarylalkyl or heteroarylalkenyl; R⁹ and R¹⁰ may be the same or different and each represents a hydrogen atom, alkyl, alkenyl, cycloalkyl, cycloalkylalkyl, heterocyclic alkyl, aryl, arylalkyl, arylalkenyl, heteroaryl, heteroarylalkyl or heteroarylalkenyl, or R⁹ and R¹⁰ of —NR⁹R¹⁰ may be combined each other to form a heterocycle;

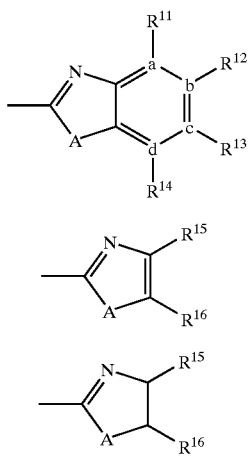

wherein a, b, c and d respectively represents a carbon atom or one of a, b, c and d represents a nitrogen atom with each of the remaining three representing a carbon atom;

R¹¹, R¹², R¹³ and R¹⁴ may be the same or different and each represents a hydrogen atom, alkyl, aryl, arylalkyl, heteroaryl, heteroarylalkyl, halogen, trifluoromethyl, cyano, nitro, —NR¹⁷R¹⁷', —NHSO₂R¹⁷, —OR¹⁷, —COOR¹⁷, —CONHSO₂R¹⁷ or —CONR¹⁷'; provided that when one of a, b, c and d represents a nitrogen atom, R¹¹, R¹², R¹³ or R¹⁴ combined to the nitrogen atom mentioned for a, b, c or d does not exist;

R¹⁵ and R¹⁶ may be the same or different and each represents a hydrogen atom, alkyl, aryl, arylalkyl, heteroaryl, heteroarylalkyl, halogen, trifluoromethyl, cyano, nitro, —N¹⁷R¹⁷', —NHSO₂R¹⁷, —OR¹⁷, —COOR¹⁷, —CONHSO₂R¹⁷ or —CONR¹⁷R¹⁷';

R¹⁷ and R¹⁷' may be the same or different and each represents a hydrogen atom, alkyl, cycloalkyl, cycloalkylalkyl, aryl, arylalkyl, heteroaryl, heteroarylalkyl or trifluoromethyl, or R¹⁷ and R¹⁷' of —NR¹⁷R¹⁷' may be combined each other to form a heterocycle;

A represents an oxygen atom, a sulfur atom or —NR¹⁸—; R¹⁸ represents a hydrogen atom, alkyl, cycloalkyl or cycloalkylalkyl;

n represents 0 or 1;

said alkyl, cycloalkyl, cycloalkylalkyl, aryl, arylalkyl, arylalkenyl, heteroaryl, heteroarylalkyl, heteroarylalkenyl, heterocycle and heterocyclic alkyl may be substituted by one or more substituents respectively.

The alkyl for R, R¹, R¹', R², R³, R⁴, R⁵, R⁶, R⁷, R⁸, R⁹, R¹⁰, R¹¹, R¹², R¹³, R¹⁴, R¹⁵, R¹⁶, R¹⁷, R¹⁷' and R¹⁸ is not particularly limited but is preferably a straight-chain or branched-chain alkyl having 1~6 carbon atoms. Specifically, said alkyl includes, for example, methyl, ethyl, n-propyl, isopropyl, n-butyl, isobutyl, sec-butyl, tert-butyl, n-pentyl, isopentyl, n-hexyl, and the like.

The cycloalkyl for R¹, R¹', R⁹, R¹⁰, R¹⁷ R¹⁷', R¹⁸ and Y is not particularly limited but is preferably a cycloalkyl having 3~7 carbon atoms. Specifically, said cycloalkyl includes, for example, cyclopropyl, cyclobutyl, cyclopentyl, cyclohexyl, cycloheptyl, and the like.

The cycloalkylalkyl for R¹, R¹', R⁹, R¹⁰, R¹⁷, R¹⁷' and R¹⁸ is not particularly limited but is preferably a group consisting of a cycloalkyl moiety which may be any of the cycloalkyl groups mentioned above and an alkyl moiety having 1~3 carbon atoms. Specifically, said cycloalkylalkyl includes, for example, cyclopropylmethyl, 2-cyclobutylethyl, 3-cyclopentylpropyl, cyclohexylmethyl, 2-cyclohexylethyl, cycloheptylmethyl, and the like.

The aryl for R¹, R¹', R⁵, R⁶, R⁷, R⁸, R⁹, R¹⁰, R¹¹, R¹², R¹³, R¹⁴, R¹⁵, R¹⁶, R¹⁷, R¹⁷' and Y is not particularly limited but includes, for example, phenyl, naphthyl; an ortho-combined bicyclic group such as indenyl, which comprises 8~10 ring atoms and at least one of the rings of which is an aromatic ring.

The arylalkyl for R¹, R¹', R², R³, R⁴, R⁵, R⁶, R⁷, R⁸, R⁹, R¹⁰, R¹¹, R¹², R¹³, R¹⁴, R¹⁵, R¹⁶, R¹⁷ and R¹⁷' is not particularly limited but is preferably a group consisting of an aryl moiety which may for example be any of said aryl groups and an alkyl moiety comprising a straight-chain or branched-chain alkyl having 1~3 carbon atoms. Specifically, said arylalkyl includes, for example, benzyl, phenethyl, 3-phenylpropyl, 1-naphthylmethyl, 2-naphthylmethyl, 2-(1-naphthyl)ethyl, 2-(2-naphthyl)ethyl, 3-(1-naphthyl)propyl, 3-(2-naphthyl)propyl, and the like.

The arylalkenyl for R⁵, R⁶ and R⁷ is not particularly limited but is preferably a group consisting of an aryl moiety which may for example be any of said aryl groups and an alkenyl moiety comprising a straight-chain or branched-chain alkenyl having 2~6 carbon atoms. Specifically, said arylalkenyl includes, for example, 3-phenyl-2-propenyl, 4-phenyl-3-butenyl, 5-phenyl-4-pentenyl, 6-phenyl-5-hexenyl, 3-(1-naphthyl)-2-propenyl, 4-(2-naphthyl)-3-butenyl, and the like.

The arylalkenyl for R⁸, R⁹ and R¹⁰ is not particularly limited but is preferably a group consisting of an aryl moiety which may for example be any of said aryl groups and an alkenyl moiety comprising a straight-chain or branched-chain alkenyl having 3~6 carbon atoms. As specific examples, 3-phenyl-2-propenyl and 4-phenyl-3-butenyl can be mentioned.

The heteroaryl for $R^1$, $R^{1'}$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{17'}$ and Y is not particularly limited but preferably includes, for example, a 5- or 6-membered cyclic group comprising a carbon atom(s) and 1~4 hetero atom(s) (oxygen, sulfur and/or nitrogen atom(s)); an ortho-combined bicyclic heteroaryl having 8~10 ring atoms which is derived from the 5- or 6-membered cyclic group mentioned just above; a benzene derivative; a group derived by combining propenylene, trimethylene or tetramethylene group with a benzene derivative; and an benzene derivative N-oxide, and the like. As specific examples, there can be mentioned pyrrolyl, furyl, thienyl, oxazolyl, isoxazolyl, imidazolyl, thiazolyl, isothiazolyl, pyrazolyl, triazolyl, tetrazolyl, 1,3,5-oxadiazolyl, 1,2,4-oxadiazolyl, 1,2,4-thiadiazolyl, pyridyl, pyranyl, pyrazinyl, pyrimidinyl, pyridazinyl, 1,2,4-triazinyl, 1,2,3-triazinyl, 1,3,5-triazinyl, benzoxazolyl, benzothiazolyl, benzimidazolyl, thianaphthenyl, isothianaphthenyl, benzofuranyl, isobenzofuranyl, chromenyl, isoindolyl, indolyl, indazolyl, isoquinolyl, quinolyl, phthalazinyl, quinoxalinyl, quinazolinyl, cinnolinyl, benzoxazinyl, and so on.

The heteroarylalkyl for $R^1$, $R^{1'}$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ and $R^{17'}$ is not particularly limited but is preferably a group consisting of a heteroaryl moiety which may for example be any of said heteroaryl groups and an alkyl moiety comprising a straight-chain or branched-chain alkyl having 1~3 carbon atoms. As specific examples, there can be mentioned 2-pyrrolylmethyl, 2-pyridylmethyl, 3-pyridylmethyl, 4-pyridylmethyl, 2-thienylmethyl, 2-(2-pyridyl)ethyl, 2-(3-pyridyl)ethyl, 2-(4-pyridyl)ethyl, 3-(2-pyrrolyl)propyl and so on.

The heteroarylalkenyl for $R^5$, $R^6$ and $R^7$ is not particularly limited but is preferably a group consisting of a heteroaryl moiety which may for example be any of said heteroaryl groups and an alkenyl moiety comprising a straight-chain or branched-chain alkenyl having 2~6 carbon atoms. As specific examples, 3-(2-pyridyl)-2-propenyl, 4-(3-pyridyl)-3-butenyl, 5-(2-pyrrolyl)-4-pentenyl, 6-(2-thienyl)-5-hexenyl, etc. can be mentioned.

The heteroarylalkenyl for $R^8$, $R^9$ and $R^{10}$ is not particularly limited but is preferably a group consisting of a heteroaryl moiety which may for example be any of said heteroaryl groups and an alkenyl moiety comprising a straight-chain or branched-chain alkenyl having 3~6 carbon atoms. As specific examples, 3-(2-pyridyl)-2-propenyl, 4-(2-pyridyl)-3-butenyl, and the like can be mentioned.

The heterocycle for $R^1$ and $R^{1'}$ is a 4- through 6-membered cyclic group having a carbon atom(s) and 1~4 hetero atom(s) (oxygen, sulfur and/or nitrogen atom(s)). This heterocycle is not particularly limited but includes, for example, azetidinyl, pyrrolidinyl, piperidinyl, piperidino, piperazinyl, morpholinyl, morpholino, thiomorpholinyl, oxothiomorpholinyl, dioxothiomorpholinyl, tetrahydropyranyl, dioxacyclohexyl, and the like.

The heterocycle represented by —$NR^3R^4$, —$NR^9R^{10}$ or —$NR^{17}R^{17'}$ is a 4- through 6-membered cyclic group comprising a carbon atom(s) and at least one nitrogen atom, optionally having other hetero atom(s) (oxygen and/or sulfur atom(s)). The heterocycle for —$NR^3R^4$, —$NR^9R^{10}$ and —$NR^{17}R^{17'}$ is not particularly limited but includes, for example, azetidinyl, pyrrolidinyl, piperidino, piperazinyl, morpholino, thiomorpholino, oxothiomorpholino, dioxothiomorpholino, and the like.

The heterocyclic alkyl for $R^1$, $R^{1'}$, $R^9$ and $R^{10}$ is not particularly limited but is preferably a group consisting of a heterocycle moiety including examples of the heterocycle for $R^1$ and $R^{1'}$ mentioned above and an alkyl moiety comprising a straight-chain or branched-chain alkyl having 1~3 carbon atoms. Specifically, said heterocyclic alkyl includes, for example, azetidinylethyl, pyrrolidinylpropyl, piperidinylmethyl, piperidinoethyl, piperazinylethyl, morpholinylpropyl, morpholinomethyl, thiomorpholinylethyl, oxothiomorpholinylethyl, dioxothiomorpholinylethyl, tetrahydropyranylpropyl, dioxacyclohexylmethyl, and the like.

The halogen for $R^8$, $R^{11}$, $R^{12}$, $R^{13}$, $R^{14}$, $R^{15}$ and $R^{16}$ is not particularly limited but includes, for example, fluorine, chlorine, bromine and iodine.

The perfluoroalkyl for $R^8$ is not particularly limited but is preferably a straight-chain or branched-chain group having 1~6 carbon atoms. As specific examples, trifluoromethyl, pentafluoroethyl, heptafluoropropyl, etc. can be mentioned.

The aminoalkyl for $R^8$ is not particularly limited but is preferably a group whose alkyl moiety comprises a straight-chain or branched-chain alkyl having 1~6 carbon atoms. As specific examples, aminomethyl, aminoethyl, aminopropyl, aminobutyl, aminopentyl, aminohexyl, etc. can be mentioned.

The alkylaminoalkyl for $R^8$ is not particularly limited but is preferably a group whose alkyl moieties respectively comprises a straight-chain or branched-chain alkyl having 1~6 carbon atoms. As specific examples, methylaminomethyl, methylaminoethyl, ethylaminopropyl, ethylaminobutyl, methylaminopentyl, methylaminohexyl, etc. can be mentioned.

The dialkylaminoalkyl for $R^8$ is not particularly limited but is preferably a group whose alkyl moieties respectively comprises a straight-chain or branched-chain alkyl having 1~6 carbon atoms. As specific examples, dimethylaminomethyl, dimethylaminoethyl, diethylaminopropyl, diethylaminobutyl, dimethylaminopentyl, dimethylaminohexyl, etc. can be mentioned.

The alkoxyalkyl for $R^8$ is not particularly limited but is preferably an alkoxyalkyl group consisting of an alkoxy moiety comprising a straight-chain or branched-chain alkoxy having 1~6 carbon atoms and an alkyl moiety comprising a straight-chain or branched-chain alkyl having 1~6 carbon atoms. As specific examples, methoxymethyl, methoxyethyl, ethoxypropyl, ethoxybutyl, methoxypentyl, methoxyhexyl, etc. can be mentioned.

The hydroxyalkyl for $R^8$ is not particularly limited but is preferably a hydroxyalkyl group whose alkyl moiety is a straight-chain or branched-chain alkyl having 1~6 carbon atoms. As specific examples, hydroxymethyl, hydroxyethyl, hydroxypropyl, hydroxybutyl, hydroxypentyl, hydroxyhexyl, etc. can be mentioned.

The alkenyl for $R^9$ and $R^{10}$ is not particularly limited but is preferably a straight-chain or branched-chain alkenyl having 3~6 carbon atoms. As specific examples, 2-propenyl, 3-butenyl, 4-pentenyl, 5-hexenyl, etc. can be mentioned.

The alkyl, cycloalkyl, cycloalkylalkyl, aryl, arylalkyl, arylalkenyl, heteroaryl, heteroarylalkyl, heteroarylalkenyl, heterocycle and heterocyclic alkyl mentioned above may each be substituted by one or more substituents mentioned below.

The substituent (s) mentioned above include, for example, halogen, hydroxyl group, nitro, cyano, trifluoromethyl, alkyl, alkoxy, alkylthio, formyl, acyloxy, oxo, phenyl, arylalkyl, —$COOR^a$, —$CH_2COOR^a$, —$OCH_2COOR^a$, —CONR$^b$R$^c$, —CH$_2$CONR$^b$R$^c$, —OCH$_2$CONR$^b$R$^c$, —COO(CH$_2$)$_2$NR$^e$R$^f$, —SO$_2$T$^1$, —CONR$^d$SO$_2$T$^1$, —NR$^e$R$^f$, —NR$^g$CHO, —NR$^g$COT$^2$, —NR$^g$COOT$^2$, —NR$^h$CQNR$^i$R$^j$, —NR$^k$SO$_2$T$^3$, —SO$_2$NR$^l$R$^m$, —SO$_2$NR$^n$COT$^4$ and the like.

The halogen mentioned above is not particularly limited but includes the species exemplified in the description of the general formula (1).

The alkyl mentioned above is not particularly limited but includes the species mentioned in the description of the general formula (1).

The arylalkyl mentioned above is not particularly limited but includes the species mentioned in the description of the general formula (1).

The alkoxy mentioned above is not particularly limited but is preferably a straight-chain or branched-chain alkoxy having 1~6 carbon atoms. As specific examples, methoxy, ethoxy, propoxy, butoxy, pentyloxy, hexyloxy, etc. can be mentioned.

The alkylthio mentioned above is not particularly limited but is preferably a straight-chain or branched-chain alkylthio having 1~6 carbon atoms. As specific examples, methylthio, ethylthio, propylthio, butylthio, pentylthio, hexylthio, etc. can be mentioned.

The acyloxy mentioned above is not particularly limited but is preferably a straight-chain or branched-chain acyloxy having 1~6 carbon atoms. As specific examples, formyloxy, acetyloxy, propionyloxy, butyryloxy, valeryloxy, pivaloyloxy, hexanoyloxy, etc. can be mentioned.

R$^a$, R$^b$, R$^c$, R$^d$, R$^e$, R$^f$, R$^g$, R$^h$, R$^i$, R$^j$, R$^k$, R$^l$, R$^m$ and R$^n$ respectively represents a hydrogen atom, alkyl or arylalkyl. The alkyl mentioned just above is not particularly limited but includes the species exemplified in the description of the general formula (1). The arylalkyl is not particularly limited, either, but includes the species exemplified in the description of the general formula (1).

—NR$^b$R$^c$, —NR$^e$R$^f$, —NR$^i$R$^j$ and —NR$^l$R$^m$ each may, taken together with the nitrogen atom to form a heterocycle. This heterocycle is not particularly limited but includes, for example, the heterocyclic groups exemplified for —NR$^3$R$^4$, —NR$^9$R$^{10}$ and —NR$^{17}$R$^{17'}$.

Furthermore, —NR$^e$R$^f$ may represent a heteroaryl having =O. The heteroaryl mentioned just above is not particularly limited but includes, for example, 2-pyrrolidinon-1-yl, succinimido, oxazolidin-2-on-3-yl, 2-benzoxazolinon-3-yl, phthalimido, cis-hexahydrophthalimido, and the like.

T$^1$, T$^2$, T$^3$ and T$^4$ each represents the same groups for R$^1$ as mentioned above. T$^1$, T$^2$, T$^3$ and T$^4$ may, further, be substituted by the substituent(s) mentioned hereinbefore.

Q represents =O or =S.

For example, when R in the general formula (1) represents alkyl or —COR$^1$ (R$^1$=alkyl), the alkyl may be substituted by —COOR$^a$.

Furthermore, —CF$_2$CONR$^9$R$^{10}$ for Z in the general formula (1) may be a group of the formula —CF$_2$CON(R$^{9'}$)—D$^1$—CONR$^{19}$R$^{20}$. In this case, R$^{9'}$ represents a hydrogen atom, alkyl or arylalkyl; R$^{19}$ and R$^{20}$ may be the same or different and each represents a hydrogen atom, alkyl, alkenyl, cycloalkyl, cycloalkylalkyl, heterocyclic alkyl, aryl, arylalkyl, arylalkenyl, heteroaryl, heteroarylalkyl or heteroarylalkenyl, or R$^{19}$ and R$^{20}$ of —NR$^{19}$R$^{20}$ may be combined each other to form a heterocycle;

D$^1$ represents a group of the following formula (iv), a group of the following formula (v) or a group of the following formula (vi);

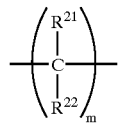

(iv)

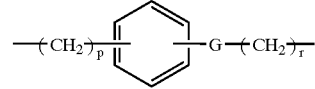

(v)

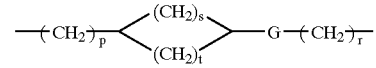

(vi)

wherein
R$^{21}$ and R$^{22}$ may be the same or different and each represents a hydrogen atom, alkyl, arylalkyl or heteroarylalkyl; R$^{21}$ and R$^{22}$ may be combined to represent a methylene chain having 2~6 carbon atoms;
m represents 1, 2, 3, 4, 5 or 6;
G represents a single bond, an oxygen atom, a sulfur atom or —NR$^{23}$—, wherein R$^{23}$ represents a hydrogen atom, alkyl or arylalkyl;
p and r may be the same or different and each represents 0, 1, 2 or 3;
s and t represent integers whose sum is equal to 1~6.

The alkyl, arylalkyl, alkenyl, cycloalkyl, cycloalkylalkyl, heterocyclic alkyl, aryl, arylalkyl, arylalkenyl, heteroaryl, heteroarylalkyl, heteroarylalkenyl and heterocycle mentioned above are respectively not particularly limited but include the groups exemplified in the description of the general formula (1). Furthermore, these groups may be respectively substituted by the substituent(s) mentioned hereinbefore.

Furthermore, —CF$_2$CONR$^9$R$^{10}$ for Z in the general formula (1) may be a group of the formula —CF$_2$CON(R$^{9''}$)—(CH$_2$)$_u$—COOR$^{24}$ or a group of the formula —CF$_2$CON(R$^{9''}$)—D$^2$. In this case, R$^{9''}$ represents a hydrogen atom, alkyl or arylalkyl; R$^{24}$ represents a hydrogen atom, alkyl, cycloalkyl, cycloalkylalkyl, aryl, arylalkyl, heteroaryl, heteroarylalkyl, heterocycle or heterocyclic alkyl; u represents 1, 2 or 3; and D$^2$ represents a group of the following formula (vii):

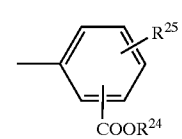

(vii)

wherein R$^{25}$ represents a hydrogen atom, alkyl, alkoxy or halogen.

The alkyl, cycloalkyl, cycloalkylalkyl, aryl, arylalkyl, heteroaryl, heteroarylalkyl, heterocycle, heterocyclic alkyl, alkoxy and halogen mentioned above are not particularly limited but respectively include the groups exemplified in the description of the general formula (1). Furthermore, these groups may have the substituent(s) mentioned hereinbefore.

The compound of the general formula (1) may exist as optically active substances as well as a racemic compound with respect to the asymmetric carbon attached to the —(CH$_2$)$_n$—Y group, and the racemic compound can be resolved into the respective optical isomers by a known procedure. Moreover, when the compound of the general formula (1) has an additional asymmetric carbon, it may exist as a mixture of diastereomers or each diastereomer. The mixture can also be separated into the respective diastereomers by a known procedure.

The compound of the general formula (1) may show polymorphism and may also exist as a plurality of tautomers. Moreover, the compound of the general formula (1) may exist as a solvate such as a ketonate or a hydrate. Therefore, the compound of the general formula (1) includes all of said stereoisomers, optical isomers, polymorphs, tautomers, solvates, and optional mixtures thereof.

In this specification, the pharmaceutically acceptable salt is not particularly limited and may include any type of salts in routine use in this field, for example, salts with mineral acids such as hydrochloric acid, sulfuric acid, nitric acid, phosphoric acid, hydrofluoric acid, hydrobromic acid, etc.; salts with organic acids such as formic acid, acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid, camphorsulfonic acid, etc.; and salts with alkali metals or alkaline earth metals, such as sodium, potassium, calcium and so on.

The compound of the general formula (1) is described as a compound having chymase inhibitory action in WO 96/33974 corresponding to U.S. Pat. No. 5,948,785, Japanese Kokai Publication Hei-10-7661, International Patent Application PCT/JP97/03839 corresponding to U.S. Pat. No. 6,080,738, and Japanese Application Hei-9-353572. The process for these compounds is also disclosed in the above patent literatures.

With regard to chymase, it is known that when the chymase activity localized in mast cells is inhibited, the release of histamine via IgE receptor from the mast cells will be suppressed (Kido H. et al., Biochem. Int., 10, 863–871, 1985) Moreover, Japanese Kokai Publication Hei-8-208654 discloses a compound having chymase inhibitory action which shows histamine release-suppressive action.

However, it was discovered by the present inventors in the course of their research that the heterocyclic amide compound of the present invention has very feeble histamine release-suppressive action (some species show no suppressive action with the use of even 1 mM), while the compound has very high chymase inhibitory action. It was, therefore, a discovery unpredictable from the knowledge of said histamine release suppressive action that the heterocyclic amide compound of the present invention has excellent IgE antibody production inhibitory action which is quite different from histamine release suppressive action, and that, based on this action, the compound is very effective as an active ingredient of the IgE antibody production inhibitor.

The IgE antibody production inhibitor of the present invention can be provided in a suitable dosage form by formulating a heterocyclic amide compound of the general formula (1) or a pharmaceutically acceptable salt thereof as an active ingredient with the suitable conventional diluents and other additives and be administered to humans or animals by the method suitable for the each dosage form.

With regard to administration of the heterocyclic amide compound of the general formula (1) or its pharmaceutically acceptable salt according to the present invention as a drug for humans or animals, it can be administered to animals including humans either as it is or in the form of a pharmaceutical composition prepared by formulating for example 0.1~99.5%, preferably 0.5~90%, of the compound or its salt in a pharmaceutically acceptable, nontoxic and inert carrier.

As the carrier mentioned just above, one or more diluents, fillers and other formulating additives which are solid, semisolid or liquid can be used. The compound or its pharmaceutically acceptable salt of the present invention is preferably administered in a unit dosage form. The compound or its pharmaceutically acceptable salt of the invention can be safely administered orally or nonorally. The nonoral administration includes local administration such as interstitial administration, subcutaneous administration, intramuscular administration, intra-arterial/venous administration, and the like.

Oral administration can be carried out by using solid or liquid dosage units prepared by the conventional procedures, such as neat powders, powders, tablets, sugar-coated tablets, capsules, granules, suspension, solution, syrup, drops, sublingual tablets, and so on.

If necessary, an oral dosage unit formulation may be microencapsulated. The same formulation may also be coated or embedded in a polymer, wax, etc. for prolonged action or sustained release.

Nonoral administration can be carried out by using liquid unit dosage forms prepared by the conventional procedures, such as a parenteral solution or suspension.

Among such administration methods, oral administration and intravenous administration by injection are preferred. Of course, administration should be made in a dosage form suited for each administration method.

The dosage of the compound of the present invention is preferably established in consideration of the patient background inclusive of age and body weight, the nature and severity of illness, etc. For oral administration of the compound to humans as an autoimmune disease suppressant, for instance, 0.1~100 mg/kg/day, preferably 0.5~10 mg/kg/day, on an adult basis can be administered in a single dose or in a few divided doses a day. For nonoral administration, although the dosage varies fairly much with different routes of administration, usually 0.001~10 mg/kg/day can be administered in a single dose or in a few divided doses a day.

The IgE antibody production inhibitor according to the first aspect of the present invention is preferably a prophylactic agent for bronchial asthma, a prophylactic agent for allergic rhinitis, a prophylactic agent for allergic dermatitis, a therapeutic agent for bronchial asthma, a therapeutic agent for allergic rhinitis or a therapeutic agent for allergic dermatitis.

When the compound of the present invention is to be administered orally as the prophylactic agent for bronchial asthma, prophylactic agent for allergic rhinitis, prophylactic agent for allergic dermatitis, therapeutic agent for bronchial asthma, therapeutic agent for allergic rhinitis or therapeutic agent for allergic dermatitis, 0.1~100 mg/kg/day, preferably 0.1~1 mg/kg/day, can be administered in a single dose or in a few divided doses a day. For nonoral administration, usually 0.001~1 mg/kg/day can be administered in a single dose or in a few divided doses a day.

The IgE antibody production inhibitor of the present invention can be administered orally or nonorally to animals except humans as well, for example domestic fowls and animals, such as chickens, swine, bovine, etc., and even to fish. For oral administration, it is generally preferable to administer a composition prepared by mixing the active compound with the conventional carriers (for example, defatted rice bran, defatted soybean meal, wheat bran, lactose, water, etc.) or a mixture of either such a composition or the compound of the invention as such with animal feedstuffs or water. The animal feedstuffs mentioned above may be the materials which are generally utilized as foods for animals, such as corn, wheat bran, rice grains, wheat grains, cottonseed cake, milo, soybean cake, fish meal, defatted rice bran, oils and fats, calcium carbonate, calcium phosphate, sodium chloride, vitamins, magnesium sulfate, iron sulfate and so forth. Some or all of these materials are used in admixture.

The concentration of the compound of the invention in a daily ration can be judiciously selected from the range of 50~2000 ppm.

Nonoral administration can be made in the same manner as said nonoral administration for humans.

The dosage of the compound of the invention is usually 10~400 mg/kg/day for oral administration and 5~200 mg/kg/day for nonoral administration, and the administration is preferably continued for several consecutive days.

The second aspect of the present invention is an autoimmune disease suppressant comprising a heterocyclic amide compound of the general formula (1) or a pharmaceutically acceptable salt thereof as an active ingredient.

The term "autoimmune disease suppressant" as used in this specification has the generally accepted meaning, which includes both a drug for prevention of an autoimmune disease and a drug for therapy of an autoimmune disease.

In the present invention, the autoimmune disease includes systemic lupus erythematosus, Hashimoto's thyroiditis, myasthenia gravis, rheumatoid arthritis, Guillain-Barré syndrome, glomerulonephritis and systemic erythematosus.

The heterocyclic amide compound of the general formula (1) or its pharmaceutically acceptable salt according to the present invention has excellent antiarthritic action, autoantibody production-inhibitory action and the like, as demonstrated in the test examples given hereunder. Therefore, the heterocyclic amide compound of the general formula (1) or its pharmaceutically acceptable salt of the invention is of great use as an active ingredient of an autoimmune disease suppressant.

The autoimmune disease suppressant of the present invention can be prepared in a suitable dosage form by formulating a heterocyclic amide compound of the general formula (1) or its pharmaceutically acceptable salt as an active ingredient with suitable conventional diluents and other additives and be administered to humans or other animals by the method suitable for the each dosage form.

The pharmaceutical production method, formulation, dosage form, dosage and the like relating to the autoimmune disease suppressant according to the second aspect of the present invention can be similar to those described hereinbefore for the first aspect of the invention.

The autoimmune disease suppressant according to the second aspect of the present invention is preferably a prophylactic agent for systemic lupus erythematosus, a prophylactic agent for Hashimoto's thyroiditis, a prophylactic agent for myasthenia gravis, a prophylactic agent for rheumatoid arthritis, a prophylactic agent for Guillain-Barré syndrome, a prophylactic agent for glomerulonephritis, a prophylactic agent for systemic erythematosus, a therapeutic agent for systemic lupus erythematosus, a therapeutic agent for Hashimoto's thyroiditis, a therapeutic agent for myasthenia gravis, a therapeutic agent for rheumatoid arthritis, a therapeutic agent for Guillain-Barré syndrome, a therapeutic agent for glomerulonephritis, or a therapeutic agent for systemic erythematosus.

It is also an aspect of the present invention to treat animals inclusive of humans by applying the IgE antibody production inhibitor or the autoimmune disease suppressant of the present invention either orally or nonorally for therapeutic and/or prophylactic purposes.

It is another aspect of the present invention to use the heterocyclic amide compound of the general formula (1) or its pharmaceutically acceptable salt of the invention for the manufacture of said IgE antibody production inhibitor and said autoimmune disease suppressant of the invention.

In as much as the IgE antibody production inhibitor and the autoimmune disease suppressant of the present invention contain said heterocyclic amide compound of the general formula (1) or its pharmaceutically acceptable salt as an active ingredient, they fall within the scope of the invention, regardless of whether they contain other ingredients.

Since the IgE antibody production inhibitor and the autoimmune disease suppressant of the present invention can be administered each in the form of a pharmaceutical composition to animals inclusive of humans, they can be called IgE antibody production inhibitor composition and autoimmune disease suppressant composition, respectively.

BEST MODE FOR CARRYING OUT THE INVENTION

The following test examples and production examples illustrate the present invention in further detail and are not intended to define the scope of the invention.

In the reference examples and examples given below, $^1$H-NMR determinations were made at 500 MHz. Chemical shifts in $^1$H-NMR were measured using TMS as the internal reference and the relative δ values were expressed in parts per million (ppm) As to coupling constants, overt components of multiplicity were expressed in Hertz units (Hz) and indicated as s (singlet), d (doublet), t (triplet), q (quartet), m (multiplet), dd (doublet of doublets), brs (broad singlet) or ABq (AB quartet). Thin-layer chromatography (TLC) and column chromatography were performed using Merck's silica gel. Concentration was made by using a rotary evaporator manufactured by Tokyo Rika Kikai, Ltd.

Reference Example 1

Synthesis of [5-benzyloxycarbonylamino-2-(4-fluorophenyl)-6-oxo-1 6-dihydro-1-pyrimidinyl] acetic acid Step (1): Hydrogen chloride was bubbled through a solution of 4-fluorobenzonitrile (50.9 g, 0.420 mol) in ethanol (500 ml) to saturation under ice-cooling and the mixture was stirred at room temperature for 21 hours. The solvent was distilled off under reduced pressure and the resulting crystals were washed with diethyl ether and dried in vacuo to give 78.8 g (yield 92%) of the objective compound ethyl 4-fluorobenzimidate hydrochloride as white crystals.

Step (2): To a solution of the objective compound of step (1) (78.8 g, 0.387 mol) in ethanol (350 ml) was added aminoacetaldehyde diethyl acetal (62 ml, 0.43 mol) with dropwise under ice-cooling, and the mixture was stirred at 5° C. for 16 hours. The ethanol was distilled off under reduced pressure and the obtained concentrate was added to 1 N-sodium hydroxide aqueous solution (750 ml) and extracted with chloroform. The extract was dried over anhydrous magnesium sulfate and the solvent was distilled off under reduced pressure to recover a colorless oil containing the objective compound N-(2,2-diethoxyethyl)-4-fluorobenzamidine.

Step (3): To a solution of the objective compound of step (2) (the crude product obtained by the above reaction) in ethanol (150 ml) was added diethylethoxymethylene malonate (86 ml, 0.43 mmol) with dropwise at room temperature. After completion of the dropwise addition, the mixture was heated to 100° C. and stirred for 3 hours. The solvent was distilled off under reduced pressure and the obtained residue was purified by silica gel column chromatography (1:1 ethyl acetate-hexane) to give 135 g [yield92% from the objective compound synthesized in step (1)] of the objective compound ethyl 1-(2,2-diethoxyethyl)-2-(4-fluorophenyl)pyrimidin-6(1H)-one-5-carboxylate as a light-yellow oil.

Step (4): To a solution of the objective compound of step (3) (135 g, 0.358 mol) in pyridine (480 ml) was added lithium iodide (120 g, 0.895 mol), and the mixture was stirred under heating at 100° C. for 16 hours. After the organic solvent was distilled off under reduced pressure, toluene (100 ml) was added, and the residual trace of pyridine was distilled off under reduced pressure. The residue was added to saturated sodium hydrogencarbonate aqueous solution (500 ml) and the compounds except the carboxylic acid was extracted with ethyl acetate. After the insoluble matter was filtered off, the aqueous layer was separated. This aqueous layer was combined with said insoluble matter, adjusted to pH 3 with 2 N-hydrochloric acid (about 1 L) and extracted with ethyl acetate. The extract was washed with saturated brine and dried over anhydrous magnesium sulfate. The solvent was then distilled off under reduced pressure to give a brownish tan-colored oil containing the objective compound 1-(2,2-diethoxyethyl)-2-(4-fluorophenyl)pyrimidin-6(1H)-one-5-carboxylic acid.

Step (5): To a solution of the objective compound of step (4) (the crude product obtained by the above reaction) and triethylamine (87.5 ml, 0.63 mol) in 1,4-dioxane (900 ml) was added diphenylphosphoryl azide (84 ml, 0.37 mol) with dropwise at room temperature. After completion of the dropwise addition, the mixture was heated to 110° C. and stirred for 2 hours. After cooling to room temperature, benzyl alcohol (44 mol, 0.43 mol) was added. This reaction mixture was heated again to 110° C. and stirred for 4 hours. After cooling to room temperature, 1,4-dioxane was distilled off under reduced pressure. The residue was added to saturated ammonium chloride aqueous solution (1 L) and extracted with ethyl acetate. The extract was washed successively with 1 N-sodium hydroxide aqueous solution and saturated brine, dried over anhydrous magnesium sulfate, and concentrated under reduced pressure. The residue was purified by silica gel column chromatography (1:2 ethyl acetate-hexane) to give 126 g of a mixture of the objective compound [5-benzyloxycarbonylamino-2-(4-fluorophenyl)-1,6-dihydro-6-oxo-1-pyrimidinyl]acetaldehyde diethyl acetal and benzyl alcohol as a light-yellow oil (yield of the objective compound 69%).

Step (6): To a solution of the objective compound of step (5) [126 g of the mixture with benzyl alcohol; 0.247 mol of the objective compound of step (5)] in THF (650 ml) was added 1 N-hydrochloric acid (500 ml), and the mixture was stirred at 70° C. for 14 hours. After cooling the reaction mixture to room temperature, THF was distilled off under reduced pressure. The obtained concentrate was adjusted to pH 7 with saturated sodium hydrogencarbonate aqueous solution and extracted with ethyl acetate. The extract was dried over magnesium sulfate and the solvent was distilled off under reduced pressure to give a white solid containing the objective compound [5-benzyloxycarbonylamino-2-(4-fluorophenyl)-1,6-dihydro-6-oxo-1-pyrimidinyl]acetaldehyde.

Step (7): To a mixture of the objective compound of step (6) (the crude product obtained by the above reaction), 2-methyl-2-propanol (900 ml) and 2-methyl-2-butene (106 ml, 1.00 mol) was added a solution of sodium dihydrogenphosphate dihydrate (180 g, 1.15 mol) and sodium chlorite (80%, 136 g, 1.20 mol) in water (400 ml), and the mixture was stirred at room temperature for 2 hours. The insoluble matter was filtered off and the organic solvent was distilled off under reduced pressure. The obtained concentrate was added to 2 N-hydrochloric acid (650 ml) and extracted with ethyl acetate. The extract was washed with saturated brine, dried over magnesium sulfate, and concentrated under reduced pressure. To the residue was added ethyl acetate-hexane (1:1) for crystallization to give 10.6 g of the title compound [5-benzyloxycarbonylamino-2-(4-fluorophenyl)-6-oxo-1,6-dihydro-1-pyrimidinyl]acetic acid as a white solid. The insoluble matter separated previously was added to 1 N-hydrochloric acid (500 ml) and extracted with ethyl acetate, and the extract was washed with saturated brine and dried over magnesium sulfate. The solvent was then distilled off under reduced pressure to give additionally 67.7 g of the title compound [5-benzyloxycarbonylamino-2-(4-fluorophenyl)-6-oxo-1,6-dihydro-1-pyrimidinyl]acetic acid as a white solid (total yield 80%).

The $^1$H-NMR and IR spectra of the above compound are shown below.

$^1$H-NMR (500 MHz, DMSO-$d_6$) δ: 13.3 (brs, 1H), 8.99 (s, 1H), 8.46 (s, 1H), 7.56 (dd, J=5.4, 8.9 Hz, 2H), 7.44 (d, J=7.2 Hz, 2H), 7.30–7.42 (m, 5H), 5.19 (s, 2H), 4.53 (s, 2H)

IR (KBr) 3650–2300, 1720, 1660, 1600 cm$^{-1}$

Reference Example 2

Synthesis of 2-amino-1-hydroxy-1-[5-(methoxycarbonyl)benzoxazol-2-yl]-3-phenylpropane Step (1): To a solution of 4-hydroxy-3-nitrobenzoic acid (15.8 g, 86.3 mmol) in 1,2-dichloroethane (150 ml) were added methanol (14 ml) and concentrated sulfuric acid (0.5 ml), and the mixture was stirred under heating at 80° C. In the course, methanol (9 ml) was added and the mixture was stirred for 21 hours. This reaction mixture was added to saturated sodium hydrogencarbonate aqueous solution (400 ml) and extracted with chloroform. The extract was washed with saturated brine, dried over magnesium sulfate, and concentrated under reduced pressure to give 11.5 g (yield 68%) of the objective compound methyl 4-hydroxy-3-nitrobenzoate as a yellow solid.

Step (2): To a solution of the objective compound of step (1) (11.4 g, 57.8 mmol) in ethyl acetate (300 ml) was added 10% palladium-carbon (1.80 g) under a nitrogen atmosphere, and the mixture was stirred under a hydrogen atmosphere at room temperature for 18 hours. The catalyst was filtered off and washed with ethyl acetate and the filtrate was concentrated under reduced pressure. The resulting solid product was washed with diethyl ether-hexane (1:1) and dried in vacuo to give 9.34 g (yield 97%) of methyl 3-amino-4-hydroxybenzoate as a light-brown solid.

Step (3): To a mixture of chloroform (10 ml) and ethanol (9.5 ml, 0.16 mol) was added acetyl chloride (10 ml, 0.14 mol) with dropwise over 10 minutes under ice-cooling. After the mixture was stirred at 0° C. for 30 minutes, a solution of the objective compound of step (2) (1.50 g, 4.83 mmol) in chloroform (10 ml) was added. After the mixture was stirred at 0° C. for 3 hours, the solvent was distilled off under reduced pressure to give a light-yellow solid. To this solid were added ethanol (35 ml) and methyl 3-amino-4-hydroxybenzoate (1.94 g, 11.6 mmol), and the mixture was stirred under heating at 90° C. for 18 hours. The solvent was distilled off under reduced pressure and the obtained concentrate was added to 0.5 N-sodium hydroxide aqueous solution (50 ml) and extracted with ethyl acetate. The extract was washed successively with 0.5 N-hydrochloric acid, saturated sodium hydrogencarbonate aqueous solution and saturated brine, dried over magnesium sulfate, and concentrated under reduced pressure. The residue was purified by silica gel column chromatography (100:1 chloroform-methanol) to give 1.80 g (yield 81%) of 2-benzyloxycarbonylamino-1-hydroxy-1-[5-(methoxycarbonyl)benzoxazol-2-yl]-3-phenylpropane as a light-brown solid.

Step (4): To a solution of the objective compound of step (3) (1.65 g, 3.58 mmol) in methanol (25 ml) was added 10% palladium-carbon (378 mg) under a nitrogen atmosphere, and the mixture was stirred under a hydrogen atmosphere at room temperature for 24 hours. The catalyst was filtered off, followed by washing with methanol, and the filtrate was concentrated under reduced pressure to give 1.14 g (yield 98%) of 2-amino-1-hydroxy-1-[5-(methoxycarbonyl)benzoxazol-2-yl]-3-phenylpropane as a light-brown solid.

The $^1$H-NMR and IR spectra of the obtained compound are shown below.

$^1$H-NMR (500 MHz, DMSO-$d_6$) δ: 8.27 (d, J=1.3 Hz, 0.4H), 8.25 (d, J=1.3 Hz, 0.6H), 8.03 (dd, J=8.6, 1.3 Hz, 0.4H), 8.02 (dd, J=8.6, 1.3 Hz, 0.6H), 7.84 (d, J=8.6 Hz, 0.4H), 7.81 (d, J=8.6 Hz, 0.6H), 7.28–7.23 (m, 4H), 7.18–7.13 (m, 1H), 4.77–4.73 (m, 1H), 3.89 (s, 3H), 3.58 (m, 0.6H), 3.50 (m, 0.4H), 3.06 (dd, J=13.6, 4.8 Hz, 0.4H), 2.88 (dd, J=13.6, 7.3 Hz, 0.6H), 2.81 (dd, J=13.6, 6.8 Hz, 0.6H), 2.65 (dd, J=13.6, 8.2 Hz, 0.4H)

IR (KBr) 3300, 1710, 1615 cm$^{-1}$

Reference Example 3

Synthesis of 2-amino-1-hydroxy-1-[5-(methoxycarbonyl)benzoxazol-2-yl]-3-phenylpropane Step (1): To a solution of 4-hydroxy-3-nitrobenzoic acid (15.8 g, 86.3 mmol) in 1,2-dichloroethane (150 ml) were added methanol (14 ml) and concentrated sulfuric acid (0.5 ml), and the mixture was stirred under heating at 80° C. In the course, methanol (9 ml) was added and the mixture was stirred for 21 hours. This reaction mixture was added to saturated sodium hydrogencarbonate aqueous solution (400 ml) and extracted with chloroform. The extract was washed with saturated brine, dried over magnesium sulfate, and concentrated under reduced pressure to give 11.5 g (yield 68%) of the objective compound methyl 4-hydroxy-3-nitrobenzoate as a yellow solid.

Step (2): To a solution of the objective compound of step (1) (11.4 g, 57.8 mmol) in ethyl acetate (300 ml) was added 10% palladium-carbon (1.80 g) under a nitrogen atmosphere, and the mixture was stirred under a hydrogen atmosphere at room temperature for 18 hours. The catalyst was filtered off, followed by washing with ethyl acetate, and the filtrate was concentrated under reduced pressure. The resulting solid product was washed with diethyl ether-hexane (1:1) and dried in vacuo to give 9.34 g (yield 97%) of methyl 3-amino-4-hydroxybenzoate as a light-brown solid.

Step (3): To a mixture of L-phenylaninol (20.2 g, 0.134 mol), sodium carbonate (21.2 g, 0.200 mol) and 1,4-dioxane (150 ml) was added a solution of. benzyloxycarbonyl chloride (19.1 ml, 0.134 mol) in 1,4-dioxane (50 ml), and the mixture was stirred at room temperature for 3 hours. To this reaction mixture was added water (300 ml) and the resulting mixture was added to ice-cooled 0.5 N-hydrochloric acid (500 ml). The resulting crystals were collected by filtration, washed with hexane, and dried to give 28.8 g (yield 76%) of the objective compound N-benzyloxycarbonyl-L-phenylalaninol as white crystals.

Step (4): To a solution of the objective compound of step (3) (10.7 g, 37.5 mmol) and triethylamine (21.3 ml, 153 mmol) in dichloromethane (100 ml) was added a solution of sulfur trioxide pyridine complex (23.9 g, 150 mmol) in dimethyl sulfoxide (DMSO) (100 ml) at −10° C. After the resulting solution was stirred at 10~20° C. for 45 minutes, it was added to saturated brine (400 ml) and extracted with diethyl ether. The extract was washed successively with 1 N-hydrochloric acid, saturated sodium hydrogencarbonate aqueous solution and saturated brine, dried over magnesium sulfate, and concentrated under reduced pressure to give 10.6 g (quantitatively) of the objective compound N-benzyloxycarbonyl-L-phenylalaninal as a white solid.

Step (5): To a solution of the objective compound of step (4) (5.00 g, 17.6 mmol) and acetone cyanohydrin (4.8 ml, 53 mmol) in dichloromethane (50 ml) was added triethylamine (1.5 ml, 11 mmol), and the mixture was stirred at room temperature for 4 hours. The solvent was distilled off under reduced pressure and the obtained concentrate was added to water (100 ml) and extracted with ethyl acetate. The extract was washed with saturated brine, dried over magnesium sulfate, and concentrated under reduced pressure. The residue was purified by silica gel column chromatography (2:1 hexane-ethyl acetate) to give 5.15 g (yield 94%) of the objective compound N-benzyloxycarbonyl-L-phenylalaninal cyanohydrine as a light-yellow solid.

Step (6): To a mixture of chloroform (10 ml) and ethanol (9.5 ml, 0.16 mol) was added acetyl chloride (10 ml, 0.14 mol) with dropwise over 10 minutes under ice-cooling. After the mixture was stirred at 0° C. for 30 minutes, a solution of the objective compound of step (5) (1.50 g, 4.83 mmol) in chloroform (10 ml) was added. The mixture was stirred at 0° C. for 3 hours, and the solvent was then distilled off under reduced pressure to give a light-yellow solid. To this solid were added ethanol (35 ml) and the objective compound of step (2) (1.94 g, 11.6 mmol), and the mixture was heated and stirred at 90° C. for 18 hours. The solvent was distilled off under reduced pressure and the obtained concentrate was added to 0.5 N-sodium hydroxide aqueous solution (50 ml) and extracted with ethyl acetate. The extract was washed successively with 0.5 N-hydrochloric acid, saturated sodium hydrogencarbonate aqueous solution and saturated brine, dried over magnesium sulfate, and concentrated under reduced pressure. The residue was purified by silica gel column chromatography (100:1 chloroform-methanol) to give 1.80 g (yield 81%) of the objective compound 2-benzyloxycarbonylamino-1-hydroxy-1-[5-(methoxycarbonyl)benzoxazol-2-yl]-3-phenylpropane as a light-brown solid.

Step (7): To a solution of the objective compound of step (6) (1.65 g, 3.58 mmol) in methanol (25 ml) was added 10% palladium-carbon (378 mg) under a nitrogen atmosphere, and the mixture was stirred under a hydrogen atmosphere at room temperature for 24 hours. The catalyst was filtered off, followed by washing with methanol, and the filtrate was concentrated under reduced pressure to give 1.14 g (yield 98%) of the title compound 2-amino-1-hydroxy-1-[5-(methoxycarbonyl)benzoxazol-2-yl]-3-phenylpropane as a light-brown solid.

The ¹H-NMR and IR spectra of the obtained compound are as follows.

¹H-NMR (500 MHz, DMSO-$d_6$) δ: 8.27 (d, J=1.3 Hz, 0.4H), 8.25 (d, J=1.3 Hz, 0.6H), 8.03 (dd, J=8.6, 1.3 Hz, 0.4H), 8.02 (dd, J=8.6, 1.3 Hz, 0.6H), 7.84 (d, J=8.6 Hz, 0.4H), 7.81 (d, J=8.6 Hz, 0.6H), 7.28–7.23 (m, 4H), 7.18–7.13 (m, 1H), 4.77–4.73 (m, 1H), 3.89 (s, 3H), 3.58 (m, 0.6H), 3.50 (m, 0.4H), 3.06 (dd, J=13.6, 4.8 Hz, 0.4H), 2.88 (dd, J=13.6, 7.3 Hz, 0.6H), 2.81 (dd, J=13.6, 6.8 Hz, 0.6H), 2.65 (dd, J=13.6, 8.2 Hz, 0.4H)

IR (KBr) 3300, 1710, 1615 cm$^{-1}$

EXAMPLE 1

Synthesis of 2-[5-amino-2-(4-fluorophenyl)-6-oxo-1,6-dihydro-1-pyrimidinyl]-N-[1-[[5-(methoxycarbonyl)benzoxazol-2-yl]carbonyl]-2-phenylethyl]acetamide (Compound 1)

Step (1): The [5-benzyloxycarbonylamino-2-(4-fluorophenyl)-6-oxo-1,6-dihydro-1-pyrimidinyl]acetic acid (1.30 g, 3.27 mmol) obtained in Reference Example 1 and the 2-amino-1-hydroxy-1-[5-(methoxycarbonyl)benzoxazol-2-yl]-3-phenylpropane (1.08 g, 3.31 mmol) obtained in Reference Example 2 were dissolved in DMF (10 ml), followed by addition of HOBT (884 mg, 6.54 mmol) and WSCI hydrochloride (752 mg, 3.92 mmol), and the mixture was stirred at room temperature for 4.5 hours. This reaction mixture was added to 0.5 N-hydrochloric acid (80 ml) and extracted with ethyl acetate. The precipitated solid was collected by filtration and dried in vacuo to give 1.26 g of 2-[5-benzyloxycarbonylamino-2-(4-fluorophenyl)-6-oxo-1,6-dihydro-1-pyrimidinyl]-N-[1-[[5-(methoxycarbonyl)benzoxazol-2-yl]hydroxymethyl]-2-phenylethyl]acetamide as a white solid. The filtrate was washed successively with saturated sodium hydrogencarbonate aqueous solution and saturated brine and concentrated in vacuo. The resulting solid was washed with diethyl ether and dried in vacuo to recover an additional 408 mg of 2-[5-benzyloxycarbonylamino-2-(4-fluorophenyl)-6-oxo-1,6-dihydro-1-pyrimidinyl]-N-[1-[[5-(methoxy-carbonyl)benzoxazol-2-yl]hydroxymethyl]-2-phenylethyl]acetamide as a light-brown solid (total amount 1.66 g, total yield 72%).

Step (2): To a solution of the objective compound of step (1) (1.56 g, 2.21 mmol) in DMSO (20 ml)-toluene (20 ml) were added WSCI hydrochloride (5.09 g, 26.6 mmol) and dichloroacetic acid (0.87 ml, 11 mmol), and the mixture was stirred at room temperature for 7 hours. This reaction mixture was added to 1 N-hydrochloric acid (100 ml) and extracted with ethyl acetate. The extract was washed with saturated sodium hydrogencarbonate aqueous solution and saturated brine. The precipitated solid was collected by filtration and dried in vacuo to give 1.06 g of 2-[5-benzyloxycarbonylamino-2-(4-fluorophenyl)-6-oxo-1,6-dihydro-1-pyrimidinyl]-N-[1-[[5-(methoxycarbonyl)benzoxazol-2-yl]carbonyl]-2-phenylethyl]acetamide as a white solid. The filtrate was concentrated under reduced pressure and the residue was purified by silica gel column chromatography (5:1 dichloromethane-ethyl acetate) to give an additional 222 mg of 2-[5-benzyloxycarbonylamino-2-(4-fluorophenyl)-6-oxo-1,6-dihydro-1-pyrimidinyl]-N-[1-[[5-(methoxycarbonyl)benzoxazol-2-yl]carbonyl]-2-phenylethyl]acetamide as a light-yellow solid (total amount 1.28 g, total yield 82%).

Step (3): To a solution of the objective compound of step (2) (462 mg, 0.657 mmol) and anisole (0.21 ml, 1.9 mmol) in dichloromethane (13 ml) was added trifluoromethanesulfonic acid (0.35 ml, 4.0 mmol) under ice-cooling, and the mixture was stirred at 0° C.~room temperature for 1 hour. Under ice-cooling, saturated sodium hydrogencarbonate aqueous solution (13 ml) was added and the mixture was further stirred for 30 minutes. This reaction mixture was added to saturated sodium hydrogencarbonate aqueous solution (50 ml) and extracted with ethyl acetate. The extract was washed with saturated brine, dried over magnesium sulfate, and concentrated under reduced pressure. The residue was purified by silica gel column chromatography (30:1 chloroform-methanol) to give 368 mg (yield 98%) of 2-[5-amino-2-(4-fluorophenyl)-6-oxo-1,6-dihydro-1-pyrimidinyl]-N-[1-[[5-(methoxycarbonyl)benzoxazol-2-yl]carbonyl]-2-phenylethyl]acetamide (Compound 1) as light-yellow crystals.

The melting point, ¹H-NMR, IR and MS spectral data of Compound 1 are shown below. mp: 208~213° C.

¹H-NMR (500 MHz, DMSO-$d_6$) δ: 8.97 (d, J=6.7 Hz, 1H), 8.51 (d, J=1.6 Hz, 1H), 8.24 (dd, J=8.7, 1.6 Hz, 1H), 8.05 (d, J=8.7 Hz, 1H), 7.35 (dd, J=8.8, 5.6 Hz, 2H), 7.28–7.17 (m, 6H), 7.08 (t, J=8.8 Hz, 2H), 5.50 (m, 1H), 5.12 (s, 2H), 4.48 (d, J=16.8 Hz, 1H), 4.41 (d, J=16.8 Hz, 1H), 3.93 (s, 3H), 3.31 (m, 1H), 2.97 (dd, J=14.1, 8.9 Hz, 1H)

IR (KBr) 3370, 1705, 1655, 1600 cm$^{-1}$

MS (SIMS, positive) m/z 570 (MH$^+$)

The human heart chymase-inhibitory activity of the obtained Compound 1 was assayed in terms of amidase inhibitory activity of human heart chymase and the efficacy of the compound was evaluated as follows.

The inhibitory activity was determined from the change in residual activity fraction of 5 nM chymase using a concentration series (<×1,<×10,<×100 equivalents) of Compound 1 in the presence of the synthetic substrate succinyl-alanyl-alanyl-prolyl-phenylalanine-p-nitroanilide at a final concentration of 2.5 mmol. Analysis of inhibitory potency was made by the least square regression of the Easson-Stedman plot utilizing bimolecular equilibrium reaction linearization (Proc. Roy. Soc. B., 121, 141, 1936). The apparent inhibition constant (Kiapp) obtained by this analysis and the inhibition constant (Ki) calculated from the final concentration of the substrate in the reaction mixture and the Km value measured separately were used to evaluate the inhibitory activity. For determination of the initial velocity of the enzymatic reaction, the amount of p-nitroaniline produced by hydrolysis of the substrate was spectrometrically estimated from the increase in the absorbance at 405 nm after subtraction of the absorbance at 650 nm. The chymase inhibitory activity of Compound 1 was calculated as the residual activity fraction in the presence of the inhibitor to the enzyme activity in the absence of the inhibitor, and the reading of measured values was completed at the point immediately under the initial velocity-guaranteeing absorbance at the substrate concentration used for the enzyme.

The reaction mixture was composed of 140 μl of Tris-HCl (100 mmol)-KCl (2 M) buffer (pH 7.5), Compound 1 dissolved in 20 μl of 10% dimethyl sulfoxide (DMSO), the substrate dissolved in 20 μl of DMSO, and 20 μl of chymase, and the total volume was 200 μl.

From the absorbance reading immediately after addition of the enzyme, the increase in absorbance was recorded at exactly equal time-intervals as a progressive curve.

The analysis of inhibitory activity was carried out from the above data, where necessary, by estimating the residual activity in the inhibitor-added sample relative to the activity in the inhibitor-free control sample from the difference between the absorbance at the end of the reaction time and the absorbance immediately after enzyme addition, or by calculating the reaction velocities in the control sample and inhibitor-added sample at a constant time interval ($\geqq 20$ minutes), shifting the velocity calculation every 10~30 minutes, averaging the values over the total reaction time, and estimating the residual activity fractions from the respective reaction velocities in the same manner.

As determined by the above human heart chymase inhibitory activity test, the chymase inhibitory activity (Ki) of Compound 1 was 0.023 μM.

EXAMPLE 2

Synthesis of 2-[5-amino-2-(3-chlorophenyl)-1 6-dihydro-6-oxo-1-pyrimidinyl]-N-[1-benzyl-3-[N-(benzyl)carbamoyl]-3,3-difluoro-2-oxopropyl] acetamide (Compound 2)

Step (1): Hydrogen chloride was bubbled through a solution of 3-chlorobenzonitrile (25.5 g, 0.185 mol) in ethanol (250 mL) to saturation under ice-cooling and the reaction mixture was stirred at room temperature for 17 hours. The solvent was distilled off under reduced pressure and the residual solid was suspended in diethyl ether (200 mL), then collected by filtration, washed with diethyl ether (200 mL) and dried in vacuo at 60° C. to give 38.3 g (94%) of ethyl 3-chlorobenzimidate hydrochloride as white crystals.

Step (2): To a solution of the objective compound of step (1) (38.0 g, 0.173 mol) in ethanol (130 mL) was added aminoacetaldehyde diethyl acetal (29 mL, 0.20 mol) with dropwise under ice-cooling, and the mixture was stirred at 5° C. for 17 hours. The ethanol was distilled off under reduced pressure and the obtained concentrate was added to 1 M sodium hydroxide aqueous solution (300 mL) and extracted with chloroform. The extract was dried over anhydrous magnesium sulfate and the solvent was distilled off under reduced pressure to give 62.6 g of a colorless clear oil containing 3-chloro-N-(2,2-diethoxyethyl)benzamidine.

Step (3): To a solution of the objective compound of step (2) (the crude product obtained by the above reaction; 62.6 g) in ethanol (75 mL) was added diethyl ethoxymethylene malonate (40 mL, 0.20 mol), and the mixture was refluxed for 3 hours. The solvent was distilled off under reduced pressure and the residue was purified by silica gel column chromatography (1:1 hexane-ethyl acetate) to give 66.4 g of ethyl 2-(3-chlorophenyl)-1(2,2-diethoxyethyl) pyrimidin-6(1H)-one-5-carboxylate as a light-yellow oil (yield 97% from ethyl 3-chlorobenzimidate hydrochloride).

Step (4): To a solution of the objective compound of step (3) (66.1 g, 0.167 mol) in pyridine (200 mL) was added lithium iodide (56.0 g, 0.418 mol), and the mixture was refluxed for 18 hours. After the pyridine was distilled off under reduced pressure, toluene (100 mL) was added, and the residual trace of pyridine was distilled off under reduced pressure. To the residue were added saturated sodium hydrogencarbonate aqueous solution (200 mL) and ethyl acetate (100 mL), and the mixture was stirred at room temperature for 30 minutes. The precipitate was filtered off and the aqueous layer was separated. The carboxylic acid in the organic layer was extracted with saturated sodium hydrogencarbonate aqueous solution (100 mL). The all aqueous layers and the precipitate separated previously were combined, adjusted to pH 4 with 2 M hydrochloric acid (about 500 mL), and extracted with ethyl acetate. The extract was washed with saturated brine, dried over anhydrous magnesium sulfate, and concentrated under reduced pressure to give 53.7 g (88%) of a deep brownish tan-colored oil containing 2-(3-chlorophenyl)-1-(2,2-diethoxyethyl)pyrimidin-6(1H)-one-5-carboxylic acid.

Step (5): To a solution of the objective compound of step (4) (53.4 g, 0.146 mol) and triethylamine (41 mL, 0.29 mol) in 1,4-dioxane (400 mL) was added diphenylphosphoryl azide (36 mL, 0.16 mol) with dropwise at room temperature. After completion of with dropwise addition, the mixture was heated and stirred at 110° C. for 2 hours. After cooling to room temperature, benzyl alcohol (20 mL, 0.19 mol) was added. The reaction mixture was heated to 110° C. again and stirred for 5 hours, followed by cooling to room temperature. The reaction mixture was concentrated under reduced pressure and the residue was added to saturated ammonium chloride aqueous solution (500 mL) and extracted with ethyl acetate. The extract was washed with 1 M sodium hydroxide aqueous solution (450 mL) and saturated brine, dried over anhydrous magnesium sulfate, and concentrated under reduced pressure. The residue was purified by silica gel column chromatography (2:1 hexane-ethyl acetate) to give 58.8 g (79%) of a 1:0.36 mixture of [5-benzyloxycarbonylamino-2-(3-chlorophenyl)-1,6-dihydro-6-oxo-1-pyrimidinyl]acetaldehyde diethyl acetal and benzyl alcohol as a light-yellow solid.

Step (6): A solution of the objective compound of step (5) (the mixture with benzyl alcohol, 58.6 g, 0.115 mol) in a mixture of THF (300 mL) and 1 M hydrochloric acid (250 mL) was heated and stirred at 70° C. for 20 hours. The THF was distilled off under reduced pressure and the concentrate was neutralized with saturated sodium hydrogencarbonate aqueous solution and extracted with ethyl acetate. The extract was dried over anhydrous magnesium sulfate and the solvent was distilled off under reduced pressure to give 52.0 g of a light-yellow oil containing [5-benzyloxycarbonylamino-2-(3-chlorophenyl)-1,6-dihydro-6-oxo-1-pyrimidinyl]acetaldehyde.

Step (7): To a mixture of the objective compound of step (6) (the crude product obtained by the above reaction; 52.0 g), 2-methyl-2-propanol (750 mL) and 2-methyl-2-butene (122 mL, 1.15 mol) was added a solution of sodium dihydrogenphosphate dihydrate (131 g, 0.840 mol) and sodium chlorite (80%, 91.0 g, 0.805 mol) in water (300 mL), and the mixture was stirred at room temperature for 3 hours. The organic solvent was distilled off under reduced pressure and the residue was added to 2 M hydrochloric acid (450 mL) and extracted with ethyl acetate. The extract was washed with saturated brine and dried over anhydrous magnesium sulfate, and the solvent was distilled off under reduced pressure to give a light-yellow oil. This oil was dissolved in ethyl acetate-hexane (1:2, 150 mL) and stirred at room temperature. The resulting crystals were collected by filtration and dried in vacuo at 60° C. to give 40.3 g of [5-benzyloxycarbonylamino-2-(3-chlorophenyl)-1,6-dihydro-6-oxo-1-pyrimidinyl]acetic acid as white crystals [yield 85% from [5-benzyloxycarbonylamino-2-(3-chlorophenyl)-1,6-dihydro-6-oxo-1-pyrimidinyl] acetaldehyde diethyl acetal].

Step (8): To a solution of N-benzyloxycarbonyl-DL-phenylalanine (155 g, 0.518 mol) in DMF (800 mL) were added mortar-pulverized potassium hydrogencarbonate (104 g, 1.04 mol) and methyl iodide (53 mL, 0.86 mol), and the mixture was stirred at room temperature for 5 hours. This reaction mixture was added to water (1800 mL) and extracted with ethyl acetate-hexane (4:1). The extract was washed successively with 2 portions of water (500 mL each), 5% sodium sulfite aqueous solution (500 ml) and saturated brine and dried over anhydrous magnesium sulfate. The solvent was distilled off under reduced pressure to give 164 g (100%) of N-benzyloxycarbonyl-DL-phenylalanine methyl ester as a colorless clear oil.

Step (9): To a solution of the objective compound of step (8) (109 g, 0.345 mol) in THF (500 mL) were added mortar-pulverized lithium chloride (29.2 g, 0.689 mol) and sodium tetrahydroborate (26.1 g, 0.690 mol). To the resulting suspension was added ethanol (1000 mL) with dropwise over 40 minutes, and the mixture was stirred at room temperature for 14 hours. To the reaction mixture was added 10% citric acid aqueous solution (700 mL), and the mixture was stirred at room temperature for 30 minutes. The organic solvent was distilled off under reduced pressure. The residue was added to water (700 mL) and extracted with dichloromethane. The extract was washed with saturated brine and dried over anhydrous magnesium sulfate, and the solvent was distilled off under reduced pressure to give white crystals. The crystals were recrystallized from ethyl acetate-hexane (1:2.7, 370 mL) to give 87.8 g (89%) of N-benzyloxycarbonyl-DL-phenylalaninol as white crystals.

Step (10): To a solution of the objective compound of step (9) (87.8 g, 0.308 mol), 2,2,6,6-tetramethyl-1-piperidinyloxy free radical (480 mg 3.07 mmol) and sodium bromide (31.7 g, 0.308 mol) in ethyl acetate (900 mL)-toluene (900 mL) were added 6% sodium hypochlorite aqueous solution (PURELOX, 410 mL, 0.34 mol) and a solution of sodium hydrogencarbonate (75 g, 0.89 mol) in water (540 mL) with dropwise over 1.5 hours under ice-cooling, and the mixture was stirred for 1 hour. This reaction mixture was extracted with ethyl acetate and the extract was washed successively with potassium iodide (2.5 g, 15 mmol)-containing 10% potassium hydrogensulfate aqueous solution (400 mL), 10% sodium thiosulfate aqueous solution (2×200 mL), 0.2 M phosphate buffer (pH 7, 500 mL) and saturated brine and dried over magnesium sulfate. The solvent was then distilled off under reduced pressure. To the residue were added ethyl acetate (150 mL) and hexane (500 mL), and the mixture was stirred at room temperature ~0° C. for 5 hours. The resulting crystal crop was collected by filtration, washed with hexane-ethyl acetate (3:1, 300 mL) and dried in vacuo to give 63.28 g (73%) of N-benzyloxycarbonyl-DL-phenylalaninal as white crystals.

Step (11): To a mixture of the objective compound of step (10) (42.8 g, 0.151 mol), zinc dust (15.9 g, 0.243 mol) and THF (105 ml) was added ethyl bromodifluoroacetate (31.6 mL, 0.246 mol) with dropwise over 2 hours at 26~49° C. The resulting mixture was stirred at room temperature for 2 hours. To this reaction mixture was added saturated ammonium chloride aqueous solution (110 mL), and the mixture was stirred for a few minutes. The obtained mixture was added to saturated ammonium chloride aqueous solution (650 mL) and extracted with ethyl acetate (500 mL, 2×300 mL). The extract was washed with saturated brine (400 mL), dried over magnesium sulfate, and concentrated under reduced pressure. The residue was purified by silica gel column chromatography (2:1 hexane-ethyl acetate) to give 56.15 g of ethyl 4-benzyloxycarbonylamino-2,2-difluoro-3-hydroxy-5-phenylpentanoate as a light-yellow oil (a mixture of diastereomers, 75%).

Step (12): To a solution of the objective compound of step (11) (12 g, 30 mmol) in THF (85 mL) was added benzylamine (16.5 mL, 0.151 mol) with dropwise over 3 minutes at room temperature, and the mixture was stirred at room temperature for 21 hours. The white precipitate was recovered by filtration and washed with ethyl acetate (3×15 mL) (2.455 g) . The filtrate was diluted with ethyl acetate (455 mL), washed successively with 1 M hydrochloric acid (3×120 mL) and saturated brine (2×120 mL), dried over magnesium sulfate, and concentrated under reduced pressure to recover a light-yellow solid residue (10.70 g). The white precipitate recovered previously and the above residue were combined (the diastereomer mixture, 13.155 g) and subjected to the next reaction.

Step (13): To a solution of the product of step (12) (13.155 g) in methanol (350 ml)-dioxane (350 mL) were added 1 M hydrochloric acid (42 mL) and 10% palladium-carbon (4.039 g, 31 wt %) under a nitrogen atmosphere, and the mixture was stirred under a hydrogen atmosphere at room temperature for 18 hours. The catalyst was filtered off and washed with methanol (10×40 mL). The filtrate and washings were pooled and concentrated under reduced pressure. The obtained residue was dissolved in ethyl acetate (500 mL) and washed with saturated sodium hydrogencarbonate aqueous solution (200 mL). The aqueous layer was extracted with ethyl acetate (2×300 mL). The obtained organic layers were pooled, washed with saturated sodium hydrogencarbonate aqueous solution (200 mL) and saturated brine (300 mL), dried over sodium sulfate, and concentrated under reduced pressure. The residue was purified by silica gel column chromatography (94:6 chloroform-methanol) to give 5.928 g of 4-amino-2,2-difluoro-3-hydroxy-5-phenylpentanoylbenzylamine as a white solid (a mixture of diastereomers; 60%, 2-step overall yield).

Step (14): To a mixture of the objective compound of step (7) (39.83 g, 96.25 mmol), the objective compound of step (13) (32.13 g, 96.09 mmol), 1-hydroxybenzotriazole (HOBT) monohydrate (29.62 g, 0.1934 mol) and DMF (590 mL) was added 1-[3-(dimethylamino)propyl]-3-ethylcarbodiimide hydrochloride (WSCIHCl) (20.57 g, 0.1073 mol), and the whole mixture was stirred at room temperature for 24 hours. This reaction mixture was added to 0.5 M hydrochloric acid (1800 mL) and extracted with ethyl acetate (1800 mL). The organic layer was filtered and the recovered precipitate was washed with ethyl acetate (50 mL, 2×20 mL) and dried in vacuo at room temperature to give 18.34 g of 2-[5-benzyloxycarbonylamino-2-(3-chlorophenyl)-1,6-dihydro-6-oxo-1-pyrimidinyl]-N-[1-benzyl-3-[N-(benzyl)carbamoyl]-3,3-difluoro-2-hydroxypropyl]acetamide as a white solid (5.1 wt % of DMF contained). The aqueous layer was extracted with ethyl acetate (2×800 mL). The organic layers were combined, washed with saturated sodium hydrogencarbonate aqueous solution (800 mL) and saturated brine (700 mL), dried over magnesium sulfate, and concentrated under reduced pressure. The residue was purified by silica gel column chromatography (98:2 chloroform-methanol) to give 59.24 g of 2-[5-benzyloxycarbonylamino-2-(3-chlorophenyl)-1,6-dihydro-6-oxo-1-pyrimidinyl]-N-[1-benzyl-3-[N-(benzyl)carbamoyl]-3,3-difluoro-2-hydroxypropyl]acetamide as a light-yellow solid (13 wt % of DMF contained). The objective compound was obtained in a total amount of 69 g (diastereomer mixture, 98%).

Step (15): To a solution of the objective compound of step (14) (69 g, 95 mmol) and WSCIHCl (99.87 g, 0.5209 mol) in DMSO (590 mL)-toluene (590 mL) was added dichloroacetic acid (15.6 mL) with drop wise over 20 minutes under ice-cooling. The resulting mixture was stirred under ice-cooling for 2.5 hours, then added to 0.5 M hydrochloric acid (1800 mL) and extracted with ethyl acetate (1800 mL, 2×800 mL). The extract was washed with saturated sodium hydrogencarbonate aqueous solution (800 mL) and saturated brine (800 mL), dried over magnesium sulfate, and concentrated under reduced pressure. The residue was purified by silica gel column chromatography (99:1 chloroform-methanol) to give 52.95 g (77%) of 2-[5-benzyloxycarbonylamino-2-(3-chlorophenyl)-1,6-dihydro-6-oxo-1-pyrimidinyl]-N-[1-benzyl-3-[N-(benzyl)carbamoyl]-3,3-difluoro-2-oxopropyl]acetamide as a white solid.

Step (16): To a solution of the objective compound of step (15) (52.93 g, 72.69 mmol) and anisole (24 mL, 0.22 mol) in dichloromethane (1000 mL) was added trifluoromethanesulfonic acid (31 mL, 0.35 mol) with dropwise over 19 minutes under ice-cooling. The resulting mixture was stirred under ice-cooling for 30 minutes. The iced-water bath was removed to let the temperature rise gradually and the reaction mixture was stirred at room temperature for 30 minutes. The reaction mixture was ice-cooled and saturated sodium hydrogencarbonate aqueous solution (800 mL) was added. The mixture was stirred until no more deposits were observed on the flask wall, and added to saturated sodium hydrogencarbonate aqueous solution (1000 mL), followed by addition of chloroform (1000 mL). The resulting mixture was divided in two portions, and each portion was extracted with ethyl acetate (1800 mL, 2×600 mL). The pooled extract was washed with saturated brine, dried over magnesium sulfate, and concentrated under reduced pressure. The residue was purified by silica gel column chromatography (96:4 chloroform-methanol) to give 41.47 g of a white solid (14 wt % of chloroform contained). This solid was recrystallized from chloroform-methanol-hexane and ethyl acetate-heptane to give 30.44 g (71%) of the title compound as a light-yellow solid.

The melting point, $^1$H-NMR, IR and MS spectra and elemental analysis of the obtained Compound 2 are shown below. mp: 115~118.5° C.

$^1$H-NMR (300 MHz, DMSO-$d_6$) δ: 9.72 (t, J=5.9 Hz, 1H), 8.83 (d, J=7.4 Hz, 1H), 7.58–7.08 (m, 15H), 5.24 (s, 2H), 4.97 (m, 1H), 4.52–4.25 (m, 4H), 3.13 (dd, J=14.3, 3.7 Hz, 1H), 2.71 (dd, J=14.3, 9.5 Hz, 1H)

IR (KBr) 3433, 3323, 3064, 3032, 1757, 1659, 1612, 1544 $cm^{-1}$

MS (ESI) m/z594 (MH$^+$)

Elemental analysis: Calcd. C=60.66; H=4.41; N=11.79. Found C=60.87; H=4.46; N=11.83.

Test Example 1

Pharmacological Testing of Compound 1

(1) Determination of IgE Antibody Titer $HgCl_2$, 1 mg/mL/kg, was administered to male BN rats (8 animals per group) subcutaneously at the back ($HgCl_2$ group). Separately, to male BN rats (8 animals per group) similarly administered with $HgCl_2$, Compounds 1~4 were administered orally in a daily dose of 30 mg/kg for 6 consecutive days beginning the $HgCl_2$ administration day (Compound 1 administration group, Compound 2 administration group, Compound 3 administration group, and Compound 4 administration group, respectively). Here, Compound 3 is 2-[5-amino-2-(3-methoxyphenyl)-6-oxo-1,6-dihydro-1-pyrimidinyl]-N-[1-[(benzoxazol-2-yl)carbonyl]-2-phenylethyl]acetamide and Compound 4 is 2-[5-amino-2-(3-methoxyphenyl)-6-oxo-1,6-dihydro-1-pyrimidin-yl]-N-[1-[[5-(methoxycarbonyl)benzoxazol-2-yl]carbonyl]-2-phenylethyl]acetamide. On day 7 following $HgCl_2$ administration, the animals were sacrificed with $CO_2$ gas, thoracotomized, and the cardiac blood was collected and centrifuged to recover the serum. The serum samples were stored at −20° C. and the IgE antibody titer was determined by the following procedure.

Anti-rat IgE monoclonal antibody [MCARE-01] [manufactured by Biochemical Industry Co., 01404] was diluted to 5 μg/mL with 0.02% $NaN_3$/PBS and an ELISA plate was coated with 50 μL of the solution at 4° C. overnight. After each well was washed, blocking was performed with 3% skim milk/TBS at room temperature for at least 1 hour. After another washing, 50 μL of the test sample diluted 200-fold with 1% BSA/TBS was added to each well, followed by 2 hours of incubation at room temperature. Each well was washed and 50 μL of ALP-labeled anti-rat κ & λ-chain monoclonal antibody (Sigma, lot 113H4804) diluted 5000-fold with 1% BSA/TBS was added. The plate was incubated at room temperature for 2 hours. Each well was washed again, and 50 μL/well of p-nitrophenyl phosphate (in 0.1 M diethanolamine, 1 mg/mL, pH 9.8) was added as the substrate solution. After color development, the reaction was stopped with an equal amount of 0.5 M NaOH and the OD was measured at the wavelength of 405 nm. As the standard rat IgE, Chemicon's rat IgE was used.

The results are shown in Table 1.

TABLE 1

| Group | Serum IgE antibody titer (mg/mL) | Inhibition rate (%) |
|---|---|---|
| $HgCl_2$ Group | 86.24 ± 7.99 | — |
| Compound 1 administration group | 62.24 ± 5.08* | 27.8 |
| Compound 2 administration group | 67.04 ± 7.57 | 22.3 |
| Compound 3 administration group | 65.25 ± 6.71* | 24.3 |
| Compound 4 administration group | 66.10 ± 8.46* | 23.4 |

Note) *p < 0.05

The above results indicate that Compound 1, Compound 3 and Compound 4 significantly inhibited the IgE antibody titer which was found to be increased significantly in the $HgCl_2$ administration group. Compound 2 was also found to show an tendency to inhibit IgE antibody production.

Test Example 2

Pharmacological Testing of Compound 1

(1) Arthritis Assay $HgCl_2$, 1 mg/mL/kg, was administered to male BN rats (8 animals per group) subcutaneously at the back every other day from day 1 to day 10, for a total of 5 times ($HgCl_2$ administration group). Separately, in parallel with the administration of $HgCl_2$, Compound 1 was administered orally in a daily dose of mg/kg every day (Compound 1 administration group). In the normal group, PBS in lieu of $HgCl_2$ was administered. On day 1, day 12, day 14, day 16 and day 18, the right and left hindpaw volumes were measured and the severity of arthritis was scored.

With regard to right and left hindpaw volumes, the left hindpaw and right hindpaw of each rat were respectively immersed in water and the increase in volume of the water was measured to calculate the rate of increase (%).

The results are shown in FIG. 1. "LEFT" represents the left hindpaw volume and "RIGHT" represents the right hindpaw volume. The ordinate represents the rate of volume increase (%). The abscissa represents the number of days from the first day of testing to the measurement day. The □ represents the normal group (PBS administration group); the ○ represents the HgCl$_2$ administration group; the ● represents the HgCl$_2$ plus Compound 1 administration group. ** indicates a significant difference from the HgCl$_2$ administration group at the significance level of not more than 0.01 and * indicates the same at the significance level of not more than 0.05.

It was found that Compound 1 significantly suppressed the rate of increase in left and right hindpaw volumes which were found to be increased significantly in the HgCl$_2$ administration group.

The arthritis severity was scored for each limb according to the following criteria and the total of scores for the four limbs (maximum score=16) and the average of the scores for 8 animals per group were calculated. 0: no symptoms 1: swelling and redness of small joints such as digital joints 2: swelling and redness of small joints such as the joints of two or more digits or comparatively large joints such as wrist and ankle joints 3: swelling and redness of the whole extremities 4: maximal swelling and redness of the whole extremities.

Figure 2:
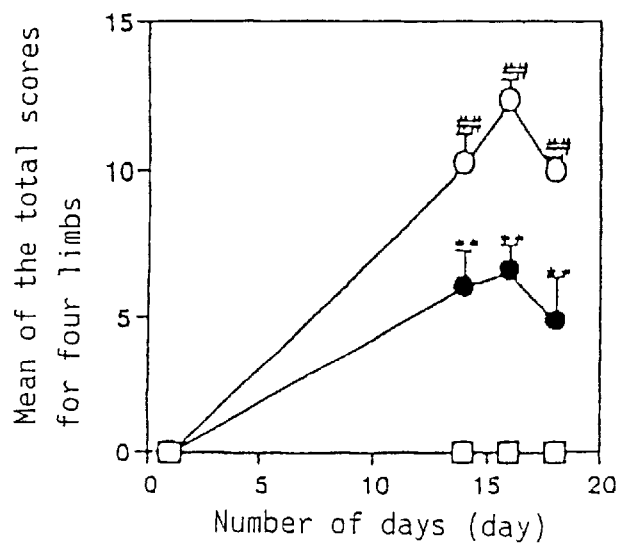
FIG. 2 is a diagram showing the antiarthritic efficacy (severity score) found in Test Example 2.

The results are shown in FIG. 2. The ordinate represents the mean of the total scores for four limbs. The abscissa represents the number of days from the beginning of the test to the measurement day. The □ represents the normal group (PBS administration group); the ○ represents the HgCl$_2$ administration group; and the ● represents the HgCl$_2$ plus Compound 1 administration group. ## indicates a significant difference from the PBS group at the significance level of not more than 0.01 and ** indicates a significant difference from the HgCl$_2$ group at the significance level of not more than 0.01.

It was clear that Compound 1 significantly reduced the arthritis severity score increased by HgCl$_2$. (2) Assay of autoantibody HgCl$_2$, 1 mg/mL/kg, was administered to male BN rats (8 animals per group) subcutaneously at the back every other day from day 1 to day 10, for a total of 5 times (HgCl$_2$ administration group). Separately, in parallel with the administration of HgCl$_2$ in the same manner as above, Compound 1 was administered orally in a daily dose of 30 mg/kg every day (Compound 1 administration group). In the normal group, PBS was administered. On day 12, day 14 and day 16, the blood was drawn from the tail vein and centrifuged to separate the serum. (2-1) Assay of anti-ssDNA antibody A 96-well plate was coated with 50 μL/well of ε-poly-L-lysine having a molecular weight of 2000–4000 (Wako Pure Chemical Industries, ECN 6644, 25 μg/mL in PBS) at room temperature for 3 hours. After the wells were washed with PBS 3 times, 50 μL/well of calf thymus single-stranded DNA (Sigma, 43H67951) diluted to 50 μg/ml with 0.02% NaN$_3$/PBS was added to the ELISA plate to coat at 4° C. overnight.

After washing, 50 μL of the test sample diluted 50-fold with 1% BSA/PBS was added to each well, and the plate was incubated at room temperature for 2 hours. As the background, wells not supplied with the test sample were provided. Amount of bound antibody was measured as the change of absorbance at 490 nm to 650 nm with the combination of peroxidase-labeled anti-rat IgE(Fc) monoclonal antibody and o-phenylendiamine (1 mg/mL) and H$_2$O$_2$ (as the control, the OD on day 1 was used). The amount of anti-ssDNA antibody was calculated as the difference (ΔOD) from that of the background.

Figure 3:
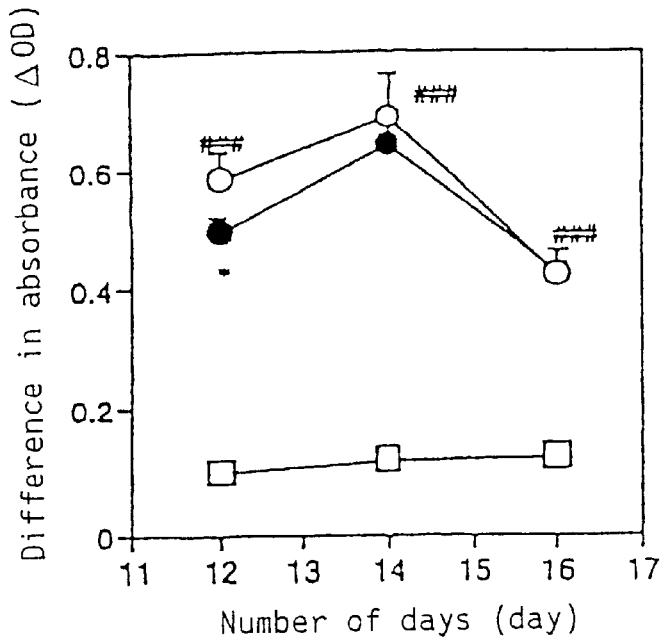
FIG. 3 is a diagram showing the measured anti-ssDNA antibody titer in Test Example 2.

The results are shown in FIG. 3. The ordinate represents the difference in absorbance (ΔOD). The abscissa represents the number of days from the beginning of the test to the measurement day. The □ represents the normal group (PBS administration group); the ○ represents the HgCl$_2$ administration group; and the * represents the HgCl$_2$ plus Compound 1 administration group. ### means a significant difference from the PBS group at the significance level of not more than 0.001 and * represents a significant difference from the HgCl$_2$ administration group at the significance level of not more than 0.05.

It was clear that Compound 1 significantly reduced the amount of anti-ssDNA antibody increased by HgCl$_2$. (2-2) Assay of anti-type II collagen antibody Type II collagen (Collagen Technology Forum, 64-50823) was diluted to 50 μg/mL with 0.02% NaN$_3$/PBS and an ELISA plate was coated with 50 μL/well at 4° C. overnight. After washing, 50 μL of the test sample diluted 50-fold with 1% BSA/PBS was added to the each well and the plate was incubated at room temperature for 2 hours. As the background, wells not supplied with the test sample were provided. Amount of bound antibody was measured as the change of absorbance at 490 nm to 650 nm with the combination of peroxidase-labeled anti-rat IgE(Fc) monoclonal antibody and o-phenylendiamine (1 mg/mL) and H$_2$O$_2$ (as the control, the OD on day 1 was used). The amount of anti-type II collagen antibody was calculated as the difference (ΔOD) from that of the background.

Figure 4:
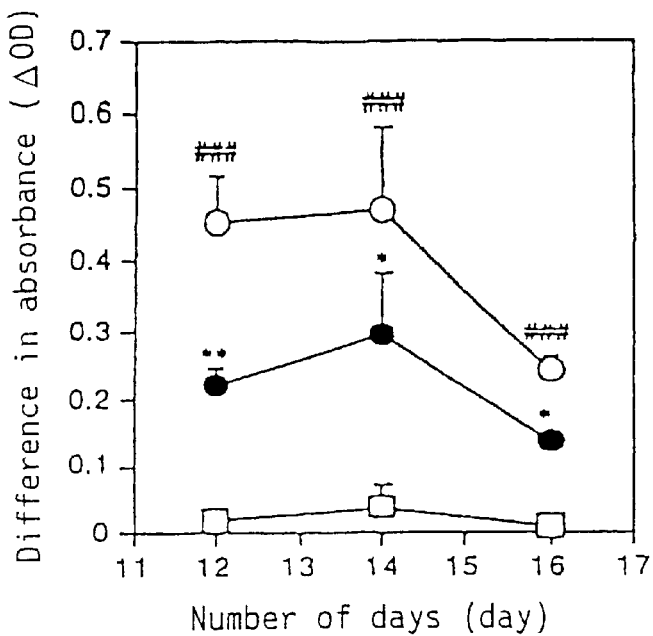
FIG. 4 is a diagram showing the measured anti-Type II collagen antibody titer in Test Example 2.

The results are shown in FIG. 4. The ordinate represents the difference in absorbance (ΔOD). The abscissa represents the number of days from the beginning of the test to the measurement day. The □ represents the normal group (PBS administration group); the ○ represents the HgCl$_2$ administration group; and the ● represents the HgCl$_2$ plus Compound 1 administration group. ### means a significant difference from the PBS group at the significance level of not more than 0.001; * indicates a significant difference from the HgCl$_2$ administration group at the significance level of not more than 0.05; and ** indicates the same at the significance level of not more than 0.01.

It is evident that Compound 1 reduced the anti-type II collagen antibody titer increased by HgCl$_2$.

Formulation Example 1

| Tablets | |
|---|---|
| (1) Compound 1 | 10 mg |
| (2) Fine granules for direct compression | |
| No. 209 (Fuji Chemical) | 46.6 mg |
| Magnesium aluminate metasilicate | 20% |
| Corn starch | 30% |
| Lactose | 50% |
| (3) Crystalline cellulose | 24.0 mg |
| (4) Carboxymethylcellulose Ca | 4.0 mg |
| (5) Magnesium stearate | 0.4 mg |

The components (1), (3) and (4) were respectively passed through a 100-mesh sieve in advance. These components (1), (3) and (4) and the component (2) were respectively dehydrated to a moisture content not over a predetermined value and then blended in the above weight proportions by means of a mixer. To the homogeneous powdery mixture thus obtained was added the component (5), and the whole mixture was stirred for a brief time (30 seconds). The resulting mixed powder was compressed (punch: 6.3 mm Ø, 6.0 mm R) to provide tablets weighing 85 mg each.

Where necessary, these tablets may be coated with the usual gastric film coating agent (e.g. polyvinyl acetal diethylaminoacetate) or an edible coloring agent.

Formulation Example 2

| Capsules | |
|---|---|
| (1) Compound 1 | 50 g |
| (2) Lactose | 935 g |
| (3) Magnesium stearate | 15 g |

The above components were respectively weighed and blended homogeneously, and the resulting mixed powder was filled in hard gelatin capsule shells, 200 mg/capsule.

Formulation Example 3

| Injection | |
|---|---|
| (1) Compound 1 hydrochloride | 5 mg |
| (2) Sucrose | 100 mg |
| (3) Physiological saline | 10 mL |

The mixed solution was filtered through a membrane filter and refiltered for bacteria-free. The filtrate was aseptically filled in vials, followed by nitrogen gas filling and sealing to provide intravenous injection.

INDUSTRIAL APPLICABILITY

The IgE antibody production inhibitor comprising the heterocyclic amide compound having the specific structure or a pharmaceutically acceptable salt thereof as an active ingredient according to the present invention has excellent IgE antibody production-inhibitory action and is of great use as a prophylactic agent for bronchial asthma, a prophylactic agent for allergic rhinitis, a prophylactic agent for allergic dermatitis, a therapeutic agent for bronchial asthma, a therapeutic agent for allergic rhinitis, a therapeutic agent for allergic dermatitis, and the like.

Furthermore, the autoimmune disease suppressant comprising the heterocyclic amide compound having the specific structure or a pharmaceutically acceptable salt thereof as an active ingredient according to the present invention has excellent antiarthritic action, autoantibody production-inhibitory action, etc. and is of great use as an autoimmune disease suppressant, particularly as a prophylactic agent for systemic lupus erythematosus, a prophylactic agent for Hashimoto's thyroiditis, a prophylactic agent for myasthenia gravis, a prophylactic agent for rheumatoid arthritis, a prophylactic agent for Guillain-Barré syndrome, a prophylactic agent for glomerulonephritis, a prophylactic agent for systemic erythematosus, a therapeutic agent for systemic lupus erythematosus, a therapeutic agent for Hashimoto's thyroiditis, a therapeutic agent for myasthenia gravis, a therapeutic agent for rheumatoid arthritis, a therapeutic agent for Guillain-Barré syndrome, a therapeutic agent for glomerulonephritis, a therapeutic agent for systemic erythematosus, and the like.

What is claimed is:

1. A method for inhibiting IgE antibody production in a patient, which comprises administrating to the patient an IgE antibody production inhibiting effective amount of a heterocyclic amide compound of the following general formula (1) or a pharmaceutically acceptable salt thereof as an active ingredient;

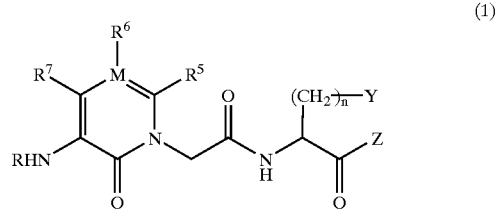

(1)

wherein R represents a hydrogen atom, alkyl, —CHO, —COOH, —CONH$_2$, —COR, —COOR$^1$, —CONHOR$^1$, —CONHR$^1$, —CONR$^1$R$^{1'}$, —CONHSO$_2$R$^1$, COSR$^1$, —COCOR$^2$, —COCOOR$^2$, —CONHCOOR$^2$, —COCONR$^3$R$^4$, —CSXR$^1$, —SO$_2$WR$^1$, —SO$_2$NR$^1$R$^{1'}$ or —SO$_2$E;

R$^1$ and R$^{1'}$ may be the same or different and each represents alkyl, cycloalkyl, cycloalkylalkyl, aryl, arylalkyl, heteroaryl, heteroarylalkyl, heterocycle or heterocyclic alkyl;

R$^2$, R$^3$ and R$^4$ may be the same or different and each represents a hydrogen atom, alkyl or arylalkyl, or R$^3$ and R$^4$ of —NR$^3$R$^4$ may be combined with each other to form a heterocycle;

X represents a single bond, an oxygen atom, a sulfur atom, or —NH—;

W represents a single bond, —NH—, —NHCO—, —NHCOO—, or —NHCONH—;

E represents hydroxyl group or amino;

R$^5$ and R$^7$ may be the same or different and each represents a hydrogen atom or alkyl, or one of R$^5$ and R$^7$ represents aryl, arylalkyl, arylalkenyl, heteroaryl, heteroarylalkyl or heteroarylalkenyl, with each of the remaining two representing a hydrogen atom;

M represents a nitrogen atom;

Y represents cycloalkyl, aryl or heteroaryl;

Z represents a hydrogen atom, —CF$_2$R$^8$, —CF$_2$CONR$^9$R$^{10}$, —CF$_2$COOR$^9$, —COOR$^9$, —CONR$^9$R$^{10}$, a group of the following formula (i), a group of the formula (ii), or a group of the following formula (iii);

R$^8$ represents a hydrogen atom, halogen, alkyl, perfluoroalkyl, aminoalkyl, alkylaminoalkyl, dialkylaminoalkyl, alkoxyalkyl, hydroxyalkyl, aryl, arylalkyl, arylalkenyl, heteroaryl, heteroarylalkyl or heteroarylalkenyl; R$^9$ and R$^{10}$ may be the same or different and each represents a hydrogen atom, alkyl, alkenyl, cycloalkyl, cycloalkylalkyl, heterocyclic alkyl, aryl, arylalkyl, arylalkenyl, heteroaryl, heteroarylalkyl or heteroarylalkenyl, or R$^9$ and R$^{10}$ of —NR$^9$R$^{10}$ may be combined with each other to form a heterocycle;

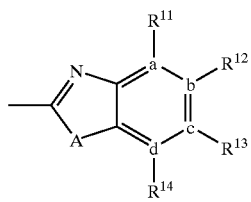

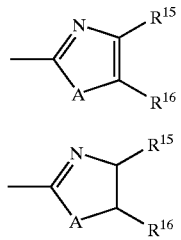

wherein
a, b, c, and d respectively represents a carbon atom or one of a, b, c, and d represents a nitrogen atom with each of the remaining three representing a carbon atom;

$R^{11}$, $R^{12}$, $R^{13}$ and $R^{14}$ may be the same or different and each represents a hydrogen atom, alkyl, aryl, arylalkyl, heteroaryl, heteroarylalkyl, halogen, trifluoromethyl, cyano, nitro, —$NR^{17}R^{17'}$, —$NHSO_2R^{17}$, —$OR^{17}$, —$COOR^{17}$, —$CONHSO_2R^{17}$ or —$CONR^{17}R^{17'}$; provided that when one of a, b, c and d represents a nitrogen atom, $R^{11}$, $R^{12}$, $R^{13}$ or $R^{14}$ combined to the nitrogen atom mentioned for a, b, c, or d does not exist;

$R^{15}$ and $R^{16}$ may be the same or different and each represents a hydrogen atom, alkyl, aryl, arylalkyl, heteroaryl, heteroarylalkyl, halogen, trifluoromethyl, cyano, nitro, —$NR^{17}R^{17'}$, —$NHSO_2R^{17}$, —$OR^{17}$, —$COOR^{17}$, —$CONHSO_2R^{17}$ or —$CONR^{17}R^{17'}$;

$R^{17}$ and $R^{17'}$ may be the same or different and each represents a hydrogen atom, alkyl, cycloalkyl, cycloalkylalkyl, aryl, arylalkyl, heteroaryl, heteroarylalkyl or trifluoromethyl, or $R^{17}$ and $R^{17'}$ of —$NR^{17}R^{17'}$ may be combined with each other to form a heterocycle;

A represents an oxygen atom, a sulfur atom or —$NR^{18}$—; $R^{18}$ represents a hydrogen atom, alkyl, cycloalkyl or cycloalkylalkyl;

n represents 0 or 1;

said alkyl, cycloalkyl, cycloalkylalkyl, aryl, arylalkyl, arylalkenyl, heteroaryl, heteroarylalkyl, heteroarylalkenyl, heterocycle and heterocyclic alkyl may be substituted by one or more substituents respectively.

2. The method according to claim 1 wherein the inhibition of IgE antibody production is intended to prevent bronchial asthma, to prevent allergic rhinitis, to prevent allergic dermatitis, to treat bronchial asthma, to treat allergic rhinitis, or to treat allergic dermatitis.

3. A method for suppressing an autoimmune disease in a patient, which comprises administrating to the patient an autoimmune disease suppressing effective amount of a heterocyclic amide compound of the following general formula (1) or a pharmaceutically acceptable salt thereof as an active ingredient;

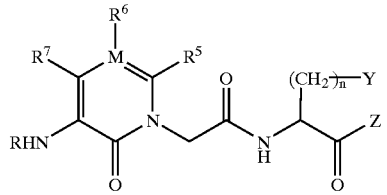

wherein R represents a hydrogen atom, alkyl, —CHO, —COOH, —$CONH_2$, —$COR^1$, —$COOR^1$, —$CONHOR^1$, —$CONHR^1$, $CONR^1R^{1'}$, —$CONHSO_2R^1$, —$COSR^1$, —$COCOR^2$, —$COCOOR^2$, —$CONHCOOR^2$, —$COCONR^3R^4$, —$CSXR^1$, —$SO_2WR_1$—$SO_2NR^1R^{1'}$ or —$SO_2E$;

$R^2$, $R^3$ and $R^4$ may be the same or different and each represents alkyl, cycloalkyl, cycloalkylalkyl, aryl, arylalkyl, heteroaryl, heteroarylalkyl, heterocycle or heterocyclic alkyl;

$R^1$ and $R^{1'}$ may be the same or different and each represents alkyl, cycloalkyl, cycloalkylalkyl, aryl, arylalkyl, heteroaryl, heteroarylalkyl, heterocycle or heterocyclic alkyl;

$R^2$, $R^3$ and $R^4$ may be the same or different and each represents a hydrogen atom, alkyl or arylalkyl, or $R^3$ and $R^4$ of —$NR^3R^4$ may be combined with each other to form a heterocycle;

X represents a single bond, an oxygen atom, a sulfur atom, or —NH—;

W represents a single bond, —NH—, —NHCO—, NHCOO— or —NHCONH—;

E represents hydroxyl group or amino;

$R^5$ and $R^7$ may be the same or different and each represents a hydrogen atom or alkyl, or one of $R^5$ and $R^7$ represents aryl, arylalkyl, arylalkenyl, heteroaryl, heteroarylalkyl or heteroarylalkenyl, with each of the remaining two representing a hydrogen atom;

M represents a nitrogen atom;

Y represents cycloalkyl, aryl or heteroaryl;

Z represents a hydrogen atom, —$CF^2R^8$, —$CF_2CONR^9R^{10}$, —$CF_2COOR^9$, —$COOR^9$, —$CONR^9R^{10}$, a group of the following formula (i), a group of the following formula (ii), or a group of the following formula (iii);

$R^8$ represents a hydrogen atom, halogen, alkyl, perfluoroalkyl, aminoalkyl, alkylaminoalkyl, dialkylaminoalkyl, alkoxyalkyl, hydroxyalkyl, aryl, arylalkyl, arylalkenyl, heteroaryl, heteroarylalkyl or heteroarylalkenyl; $R^9$ and $R^{10}$ may be the same or different and each represents a hydrogen atom, alkyl, alkenyl, cycloalkyl, cycloalkylalkyl, heterocyclic alkyl, aryl, arylalkyl, arylalkenyl, heteroaryl, heteroarylalkyl or heteroarylalkenyl, or $R^9$ and $R^{10}$ of —$R^9R^{10}$ may be combined with each other to form a heterocycle;

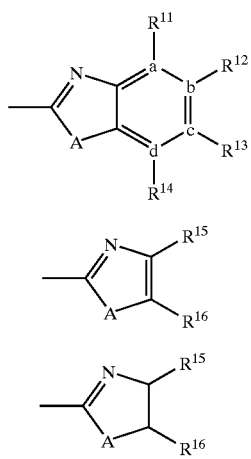

wherein a, b, c and d respectively represents a carbon atom or one of a, b, c and d represents a nitrogen atom with each of the remaining three representing a carbon atom;

$R^{11}$, $R^{12}$, $R^{13}$ and $R^{14}$ may be the same or different and each represents a hydrogen atom, alkyl, aryl, arylalkyl, heteroaryl, heteroarylalkyl, halogen, trifluoromethyl, cyano, nitro, —$NR^{17}R^{17'}$, —$NHSO_2R^{17}$, —$OR^{17}$, —$COOR^{17}$, —$CONHSO_2R^{17}$, or —$CONR^{17}R^{17'}$; provided that when one of a, b, c and d represents a nitrogen atom, $R^{11}$, $R^{12}$, $R^{13}$ or $R^{14}$ combined to the nitrogen atom mentioned for a, b, c or d does not exits;

$R^{15}$ and $R^{16}$ may be the same or different and each represents a hydrogen atom, alkyl, aryl, arylalkyl, heteroaryl, heteroarylalkyl, halogen, trifluoromethyl, cyano, nitro, —$NR^{17}R^{17'}$, —$NHSO_2R^{17}$, —$OR^{17}$, —$COOR^{17}$, —$CONHSO_2R^{17}$ or —$CONR^{17}R^{17'}$;

$R^{17}$ and $R^{17'}$ may be the same or different and each represents a hydrogen atom, alkyl, cycloalkyl, cycloalkylalkyl, aryl, arylalkyl, heteroaryl, heteroarylalkyl or trifluoromethyl, or $R^{17}$ and $R^{17'}$ of —$NR^{17}R^{17'}$ may be combined with each other to form a heterocycle;

A represents an oxygen atom, a sulfur atom or —$NR^{18}$—; $R^{18}$ represents a hydrogen atom, alkyl, cycloalkyl or cycloalkylalkyl;

n represents 0 or 1;

said alkyl, cycloalkyl, cycloalkylalkyl, aryl, arylalkyl, arylalkenyl, heteroaryl, heteroarylalkyl, heteroarylalkenyl, heterocycle and heterocyclic alkyl may be substituted by one or more substituents respectively.

4. The method according to claim 3 wherein the suppression of an autoimmune disease is intended to prevent systemic lupus erythematosus, to prevent Hashimoto's thyroiditis, to prevent myasthenia gravis, to prevent rheumatoid arthritis, to prevent Guillain-Barré syndrome, to prevent glomerulonephritis, to prevent systemic erythematosus, to treat systemic lupus erythematosus, to treat Hashimoto's thyroiditis, to treat myasthenia gravis, to treat rheumatoid arthritis, to treat Guillain-Barré syndrome, to treat glomerulonephritis, or to treat systemic erythematosus.

5. The method according to claim 1 wherein R represents hydrogen;

$R^5$ represents phenyl, which may be substituted by one or more of halogen or alkoxy;

$R^7$ represents hydrogen;

Y represents phenyl; and n represents 1.

6. The method according to claim 1 wherein said heterocyclic amide compound is selected from the group consisting of 2-[5-amino-2-(4-fluorophenyl)-6-oxo-1,6-dihydro-1-pyrimidinyl]-N-[1-[5-methoxycarbonyl(benzoxazol-2-yl) carbonyl]-2-phenylethyl]acetamide; 2-[5-amino-2-(3-chlorophenyl)-6-oxo-1,6-dihydro-1-pyrimidinyl]-N-[1-benzyl-3-[N-(benzyl)carbamoyl]-3,3-difluoro-2-oxopropyl] acetamide; 2-[5-amino-2-(3-methoxyphenyl)-6-oxo-1,6-dihydro-1-pyrimidinyl]-N-[1-[(benzoxazol-2-yl)carbonyl]-2-phenylethyl]acetamide; and 2-[5-amino-2-(3-methoxyphenyl)-6-oxo-1,6-dihydro-1-pyrimidinyl]-N-[1-[5-(methoxycarbonyl)benzoxazol-2-yl]carbonyl]-2-phenylethyl]acetamide.

7. The method according to claim 1 wherein $R^5$ is alkyl, aryl, arylalkyl, arylalkenyl, heteroaryl, heteroarylalkyl or heteroarylalkenyl.

8. The method according to claim 7 wherein $R^5$ is phenyl, naphthyl or indenyl.

9. The method according to claim 8 wherein the phenyl, naphthyl or indenyl is substituted by halogen, hydroxyl group, nitro, cyano, trifluoromethyl, alkyl, alkoxy, alkylthio, formyl, acyloxy, oxo, phenyl, arylalkyl, —$COOR^a$, —$CH_2COOR^a$, —$OCH_2COOR^a$, —$CONR^bR^c$, —$CH_2CONR^bR^c$, —$OCH_2CONR^bR^c$, —$COO(CH_2)_2NR^eR^f$, —$SO_2T^1$, —$CONR^dSO_2T^1$, —$NR^eR^f$, —$NR^gCHO$, —$NR^gCOT^2$, —$NR^gCOOT^2$, —$NR^hCQNR^iR^j$, —$NR^kSO_2T^3$, —$SO_2NR^lR^m$, or —$SO_2NR^nCOT^4$, wherein each of $R^a$, $R^b$, $R^c$, $R^d$, $R^e$, $R^f$, $R^g$, $R^h$, $R^i$, $R^j$, $R^k$, $R^l$, $R^m$, and $R^n$, which may be the same or different, represents a hydrogen atom, alkyl or arylalky; —$NR^bR^c$, —$NR^eR^f$, —$NR^iR^j$ and —$NR^lR^m$ each may, taken together with the nitrogen atom to form a heterocycle; —$NR^eR^f$ may represent a heteroaryl having =O;

wherein $T^1$, $T^2$, $T^3$ and $T^4$, which may be the same or different, each represents alkyl, cycloalkyl, cycloalkyalky, aryl, arylalkyl, heteroaryl, heteroarylalkyl, heterocyclic or heterocyclicalkyl; and wherein Q represents =O or =S.

10. The method according to claim 5 wherein Z represents —$CF_2CONR^9R^{10}$ or a group of the following formula (i):

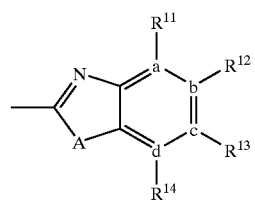

UNITED STATES PATENT AND TRADEMARK OFFICE
CERTIFICATE OF CORRECTION

PATENT NO.   : 6,528,514 B1
DATED        : March 4, 2003
INVENTOR(S)  : Fujio Kobayashi et al.

It is certified that error appears in the above-identified patent and that said Letters Patent is hereby corrected as shown below:

Column 30,
Line 22, delete "-COR" and insert -- -COR$^1$ --;

Column 32,
Lines 22-25, delete "$R^2$, $R^3$ and $R^4$ may be the same or different and each represents alkyl, cycloalkyl, cycloalkylalkyl, aryl, arylalkyl, heteroaryl, heteroarylalkyl, heterocycle, or heterocyclic alkyl;"

Column 34,
Line 46, delete "cycloalkyalky" and insert -- cycloalkylalkyl --;
Line 47, delete "heterocyclic" and insert -- heterocycle -- and delete "heterocyclicalkyl" and insert -- heterocyclic alkyl --.

Signed and Sealed this

Second Day of December, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,528,514 B1  Page 1 of 1
DATED : March 4, 2003
INVENTOR(S) : Fujio Kobayashi et al.

It is certified that error appears in the above-identified patent and that said Letters Patent is hereby corrected as shown below:

Column 32,
Line 21, delete "-$SO_2$ $WR_1$" and insert -- -$SO_2$ $WR^1$, --

Column 34,
Lines 20-23, delete "2-[5-amino-2-(3-methoxyphenyl)-6-oxo-1,6-dihydro-1-pyrimidinyl]-N-[1-[5-methoxycarbonyl)benzoxazol-2-yl]carbonyl]-2-phenylethyl] acetamide." and insert -- 2-[5-amino-2-(3-methoxyphenyl)-6-oxo-1,6-dihydro-1-pyrimidinyl]-N-[1-[[5-methoxycarbonyl)benzoxazol-2-yl]carbonyl]-2-phenylethyl] acetamide. --

Signed and Sealed this

Eighth Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,528,514 B1
DATED : March 4, 2003
INVENTOR(S) : Fujio Kobayashi et al.

It is certified that error appears in the above-identified patent and that said Letters Patent is hereby corrected as shown below:

Column 30,
Line 24, delete "COSR$^1$" and insert -- -COSR$^1$ --.

Signed and Sealed this

Seventh Day of September, 2004

JON W. DUDAS
*Director of the United States Patent and Trademark Office*